United States Patent
Braganza et al.

(10) Patent No.: US 11,896,403 B2
(45) Date of Patent: Feb. 13, 2024

(54) IMPLANTABLE MEDICAL DEVICE USING TEMPERATURE SENSOR TO DETERMINE INFECTION STATUS OF PATIENT

(71) Applicant: Medtronic, Inc., Minneapolis, MN (US)

(72) Inventors: Ameet Braganza, Santa Barbara, CA (US); Mark T. Marshall, Forest Lake, MN (US); Teresa A. Whitman, Dayton, MN (US); Robert W. Stadler, Shoreview, MN (US); Brian B. Lee, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 47 days.

(21) Appl. No.: 16/751,929

(22) Filed: Jan. 24, 2020

(65) Prior Publication Data

US 2021/0228160 A1 Jul. 29, 2021

(51) Int. Cl.
*A61B 5/00* (2006.01)
*A61B 5/01* (2006.01)
*A61B 5/07* (2006.01)

(52) U.S. Cl.
CPC .............. *A61B 5/7282* (2013.01); *A61B 5/01* (2013.01); *A61B 5/686* (2013.01); *A61B 5/7203* (2013.01);
(Continued)

(58) Field of Classification Search
CPC ......... A61B 5/0031; A61B 5/01; A61B 5/024; A61B 5/076; A61B 5/1118; A61B 5/4842; A61B 5/686; A61B 5/7203; A61B 5/7275; A61B 5/725; A61B 5/7282; A61B 2562/04; A61N 1/3655; A61N 1/37258; A61N 1/3702; A61N 1/37282
See application file for complete search history.

(56) References Cited

U.S. PATENT DOCUMENTS

| 6,248,080 B1 | 6/2001 | Miesel et al. |
| 7,766,862 B2 | 8/2010 | Gerber et al. |

(Continued)

FOREIGN PATENT DOCUMENTS

| WO | 2009055865 A1 | 5/2009 | |
| WO | 2015200704 A1 | 12/2015 | |
| WO | WO-2016102971 A2 * | 6/2016 | ........... A61B 5/4325 |

OTHER PUBLICATIONS

International Search Report and Written Opinion of International Application No. PCT/US2020/066294, dated Apr. 14, 2021, 10 pp.

(Continued)

*Primary Examiner* — Alex M Valvis
*Assistant Examiner* — Anna Roberts
(74) *Attorney, Agent, or Firm* — Shumaker & Sieffert, P.A.

(57) ABSTRACT

Techniques for detecting infections in a patient in relation to temperature values obtained from implantable temperature sensors are described. An example implantable temperature sensor may be included within a housing of an implantable medical device (IMD). In some examples, the temperature sensor may determine a plurality of temperature values over time. Processing circuitry of the IMD or of an external device may smooth the temperature values and apply an infection detection model to the smoothened temperature signal to determine an infection status of the patient.

17 Claims, 16 Drawing Sheets

(52) U.S. Cl.
CPC ............... *A61B 5/725* (2013.01); *A61B 5/076* (2013.01); *A61B 2562/04* (2013.01)

(56) References Cited

U.S. PATENT DOCUMENTS

| | | | |
|---|---|---|---|
| 8,551,092 | B2 | 10/2013 | Morgan et al. |
| 8,583,224 | B2 | 11/2013 | Lee et al. |
| 2008/0064980 | A1 | 3/2008 | Lee et al. |
| 2008/0262332 | A1 | 10/2008 | Gerber et al. |
| 2008/0262378 | A1* | 10/2008 | Gerber ................. A61B 5/6846 600/549 |
| 2008/0262379 | A1 | 10/2008 | Gerber et al. |
| 2008/0262380 | A1 | 10/2008 | Gerber et al. |
| 2008/0262580 | A1 | 10/2008 | Gerber et al. |
| 2009/0024054 | A1 | 1/2009 | Lazarus et al. |
| 2009/0198146 | A1 | 8/2009 | Gerber et al. |
| 2014/0236029 | A1* | 8/2014 | Averina ............. A61B 5/02055 600/508 |
| 2015/0328459 | A1* | 11/2015 | Chin .................... A61N 1/3655 607/21 |
| 2016/0029952 | A1 | 2/2016 | Hunter |
| 2020/0069247 | A1 | 3/2020 | Hunter |
| 2020/0357513 | A1 | 11/2020 | Katra et al. |

OTHER PUBLICATIONS

Mela et al., "Long-Term Infection Rates Associated With the Pectoral Versus Abdominal Approach to Cardioverter-Defibrillator Implants," The American Journal of Cardiology, vol. 88, No. 7, Oct. 1, 2001, 4 pp.

Muhammad et al., "Mortality and Cost Associated With Cardiovascular Implantable Electronic Device Infections," American Medical Association, Archives of internal medicine, vol. 141, No. 20, Sep. 12, 2011, 8 pp.

Baman et al., "Risk Factors for Mortality in Patients With Cardiac Device-Related Infection," American Heart Association, Circulation: Arrhythmia and Electrophysiology, Jan. 7, 2009, 6 pp.

Aljabri et al., "Management of Device Infections," Cardiac Electrophysiology Clinics, vol. 10, Issue 1, doi. org/10.1016/j.ccep.2017.11.016, Mar. 2018, pp. 153-162.

Asfandyar et al., "Validation of Commercially Available Infrared Thermometers for Measuring Skin Surface Temperature Associated with Deep and Surrounding Wound Infection," Advances in Skin & Wound Care, vol. 28, No. 1, Jan. 2015, pp. 11-16.

Decoene et al., "Endothelium-dependent relaxation is impaired after endotoxic shock in rabbits," American Journal of Respiratory and Critical Care Medicine, Supplement, vol. 155, No. 4, Pt. 2, A926, Apr. 1997, 4 pp.

Fakhro et al., "Treatment of Infected Cardiac Implantable Electronic Devices," Seminars in Plastic Surgery, vol. 30, No. 2, doi: 10.1055/s-0036-1580733, May 2016, pp. 60-65.

Kuebler et al., "Roles of L-Selection in Leukocyte Sequestration in Lung capillaries in a Rabbit Model of Endotoxemia," The American Journal of Respiratory and Critical Care Medicine, vol. 161, Issue 1, doi.org/10.1164/ajrccm. 161.1.9901039, Jan. 1999, pp. 36-43.

Kumar et al., "Hemodynamic and Metabolic Manifestations of Acute Endotoxin Infusion in Pigs with and without the Malignant Hyperthermia Mutation," Anesthesiology, vol. 91, No. 3, Sep. 1999, pp. 833-838.

Lambert et al., "Cardiac implantable electronic device infection," Cleveland Clinic Journal of Medicine, vol. 84, Supplement 3, doi:10.3949/ccjm.84.s3.05, Dec. 2017, pp. 47-53.

Looser et al., "Systemic infection due to subctaneous implantable cardioverter-defibrillator implantation: Importance of early recognition and treatment of device pocket-related complications," Heart Rhythm Society, vol. 3, No. 1, DOI: https://doi.org/10.1016/j.hrcr.2016.08.014, Jan. 2017, pp. 40-42.

Mathison et al., "The Clearance, Tissue Distribution, and Cellular Localization of Intravenously Injected Lipopolysaccharide in Rabbits," The Journal of Immunology, vol. 123, No. 56, Nov. 1, 1979, pp. 2133-2143.

Musley et al., "Role of Device Temperature Sensor And Impedance In A Rabbit Model Of Bacterial Pocket Infection Versus Systemic Endotoxemia," [Abstract], CTI Meeting Technology, The Online Abstract Submission System, 2021-SS-A-8876-AHA, Accessed on Apr. 29, 2021, 2 pp.

Parrillo, "Pathogenic mechanisms of septic shock," New England Journal of Medicine, vol. 328, No. 20, May 1993, pp. 1471-1477.

Siegert et al., "Mechanism for Fever Induction in Rabbits, "American Society for Microbiology, Infection and Immunity, vol. 14, No. 5, Nov. 1976, pp. 1130-1137.

Sohail et al., "Management and Outcome of Permanent Pacemaker and Implantable Cardioverter-Defibrillator Infections," Elsevier, Journal of the American College of Cardiology, vol. 49, No. 18, doi: 10.1016/j.jacc.2007.01.072, May 2007, pp. 1851-1859.

Tarakji et al., "Cardiac Implantable Electronic Device Infection in Patients at Risk," PMC, Arrhythmia & Electrophysiology Review, vol. 5, No. 1, doi:10.15420/aer.2015.27.2, May 2016, pp. 65-71.

Tarakji et al., "Cardiac implantable electronic device infections: Presentation, management, and patient outcomes," Heart Rhythm Society, Heart Rhythm, vol. 7, May 2010, pp. 1043-1047.

Tarakji et al., "Hemotoma and Cardiac Implantable Electronic Device Infection. Insights from the Wrap-It Trail," [Poster], JACC, vol. 77, Issue 18, May 11, 2021, p. 248.

Venta et al., "Thermographic Imaging of Postoperative Inflammation Modified by Anti-Inflammatory Pretreatment," Journal of Oral Maxillofac Surgery, vol. 59, No. 2, doi: 10.1053/joms.2001.20483, Feb. 2001, pp. 145-148.

Von Eiff et al., "Infections Associated with Medical Devices—Pathogenesis, Management and Prophylaxis," Drugs, vol. 65, No. 2, Jan. 2005, pp. 179-214.

* cited by examiner

IMPLANTABLE MEDICAL DEVICE USING TEMPERATURE SENSOR TO DETERMINE INFECTION STATUS OF PATIENT

FIELD

The disclosure relates, inter alia, to implantable medical devices and, more particularly, it relates to systems, devices and methods for monitoring infection, such as infection in proximity to medical devices implanted in patients.

BACKGROUND

Infection associated with implantation of medical devices is a serious health and economic concern. Today, infections associated with implanted medical devices are not very common due to care and precautions taken during surgical implantation of the devices. However, when an infection associated with an implanted medical device (IMD) does occur, explanting the device is often the only appropriate course of action.

For IMDs having a battery powered component, such as implantable cardiac pacemakers, cardioverter/defibrillators having pacing capabilities, other electrical stimulators including spinal cord, deep brain, nerve, and muscle stimulators, infusion devices, cardiac and other physiologic monitors, cochlear implants, etc., the battery powered component is typically enclosed in a housing that is implanted at a surgically prepared site, referred to as a "pocket". Associated devices, such as elongated medical electrical leads or drug delivery catheters, extend from the pocket to other subcutaneous sites or deeper into the body to organs or other implantation sites.

Surgical preparation and implantation are conducted in a sterile field, and the IMD components are packaged in sterile containers or sterilized prior to introduction into the sterile field. However, despite these precautions, there always is a risk of introduction of microbes into the pocket. Surgeons therefore typically apply disinfectant or antiseptic agents to the skin at the surgical site prior to surgery, directly to the site before the incision is closed, and prescribe oral antibiotics for the patient to ingest during recovery.

Despite these precautions, infections can occur. In addition, once the pocket becomes infected, the infection can migrate along the lead or catheter to locations in which the lead or catheter is implanted. Removal of a chronically implanted lead or catheter, e.g., in response to such an infection, can be difficult. Accordingly, aggressive systemic drug treatment is prescribed to treat such infections. However, early detection of infections associated with implanted medical devices may allow for earlier intervention, resulting in fewer device explants.

SUMMARY

This disclosure describes techniques for determining an infection status of a patient (e.g., bacterial infections, device pocket infections, etc.) based on temperature measurements determined from at least one temperature sensing device disposed within a body of a patient. The techniques may be implemented by an implantable medical device (IMD) that comprises the at least one temperature sensing device. The techniques of this disclosure may be implemented by any number of computing devices (e.g., an IMD or remote computing device, such as a network device) using temperature measurements obtained by the temperature sensing device. In some examples, processing circuitry of the IMD or remote computing device may determine whether an infectious agent, such as a harmful bacteria, has infiltrated a device pocket where an IMD is implanted in the body of a patient. In particular, the device may utilize particular signal processing techniques and algorithms that allow processing circuitry to accurately determine infections by conditioning signals and applying various detection models, such as a sliding window detection model or a multiple low-pass-filter integration model. Such detection models may allow processing circuitry to accurately distinguish increases in temperature signals that are caused by device pocket infections, for example, as opposed to an increase in temperature caused by daily fluctuations in temperature.

In one example, the sliding window detection model includes a rate of change detection model that uses at least two temperature data points of a smoothened temperature signal to determine a slope value in one sliding window. In some examples, the sliding window detection model may include a maximum-minimum detection model, where multiple sliding windows of temperature data points are used. In any event, the temperature data points are obtained from a temperature sensing device of an IMD. In another example, processing circuitry may compare smoothened temperature signals obtained through use of filters having different cutoff frequencies. In any case, monitoring of infection through the use of sensors, such as temperature sensing devices of an IMD, can provide information indicative of infection.

In this way, processing circuitry may detect local temperature changes at the IMD that may not be reflected in core body temperature monitors. That is, the temperature of an IMD may have a consistently lower temperature than core temperature by approximately 1-2 degrees with the IMD temperature lagging (e.g., following) relative changes in core temperature. However, in cases including infections in a device pocket, the IMD temperature may lead the core body temperature, and in some instances, may increase without any significant change in core body temperature. As such, processing circuitry may need to employ algorithms that may discern temperature changes caused by different unremarkable events compared to changes in pocket temperature caused by device pocket infections. In accordance with various techniques of this disclosure, processing circuitry may accurately determine various different types of infections from other types of infections using algorithms summarized above and described below.

In one example, the disclosure provides a system for determining an infection status of a patient. The system comprises an implantable medical device (IMD) comprising at least one temperature sensing device. The system further comprises processing circuitry configured to at least determine, via the temperature sensing device, a plurality of temperature values over time; smooth the plurality of temperature values determined over time to create a smoothened temperature signal representing changes in the plurality of temperature values over time; apply an infection detection model to the smoothened temperature signal to determine an infection indication value, the infection detection model comprising one or more of a sliding window detection model or multiple low-pass-filter integration model; compare the infection indication value to a threshold; and determine, based at least in part on the infection indication value satisfying the threshold, an infection status of a patient.

In another example, the disclosure provides a method for determining an infection status of a patient, the method comprising determining, via a temperature sensing device of an implantable medical device (IMD), a plurality of temperature values over time; smoothing the plurality of temperature values determined over time to create a smoothened temperature signal representing changes in the plurality of temperature values over time; applying an infection detection model to the smoothened temperature signal to determine an infection indication value, the infection detection model comprising one or more of a sliding window detection model or multiple low-pass-filter integration model; comparing the infection indication value to a threshold; and determining, based at least in part on the infection indication value satisfying the threshold, an infection status of a patient.

In another example, the disclosure provides a computer-readable storage-medium having stored thereon instructions that, when executed, cause one or more processors to at least determine, via a temperature sensing device of an implantable medical device (IMD), a plurality of temperature values over time; smooth the plurality of temperature values determined over time to create a smoothened temperature signal representing changes in the plurality of temperature values over time; apply an infection detection model to the smoothened temperature signal to determine an infection indication value, the infection detection model comprising one or more of a sliding window detection model or multiple low-pass-filter integration model; compare the infection indication value to a threshold; and determine, based at least in part on the infection indication value satisfying the threshold, an infection status of a patient.

The disclosure also provides means for performing any of the techniques described herein, as well as non-transitory computer-readable media comprising instructions that cause a programmable processor to perform any of the techniques described herein.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

Like reference characters denote like elements throughout the description and figures.

DETAILED DESCRIPTION

Implantable medical devices (IMDs) can sense and monitor signals and use those signals to determine various conditions of a patient and/or provide therapy to the patient. Example IMDs include monitors, such as the Reveal LINQ™ Insertable Cardiac Monitor, available from Medtronic plc. Such IMDs may facilitate relatively longer-term monitoring of patients during normal daily activities and may periodically transmit collected data to a network service, such as the Medtronic CareLink® Network, developed by Medtronic, Inc., of Minneapolis, Minn., or some other network linking patient 4 to a clinician.

Figure 1:
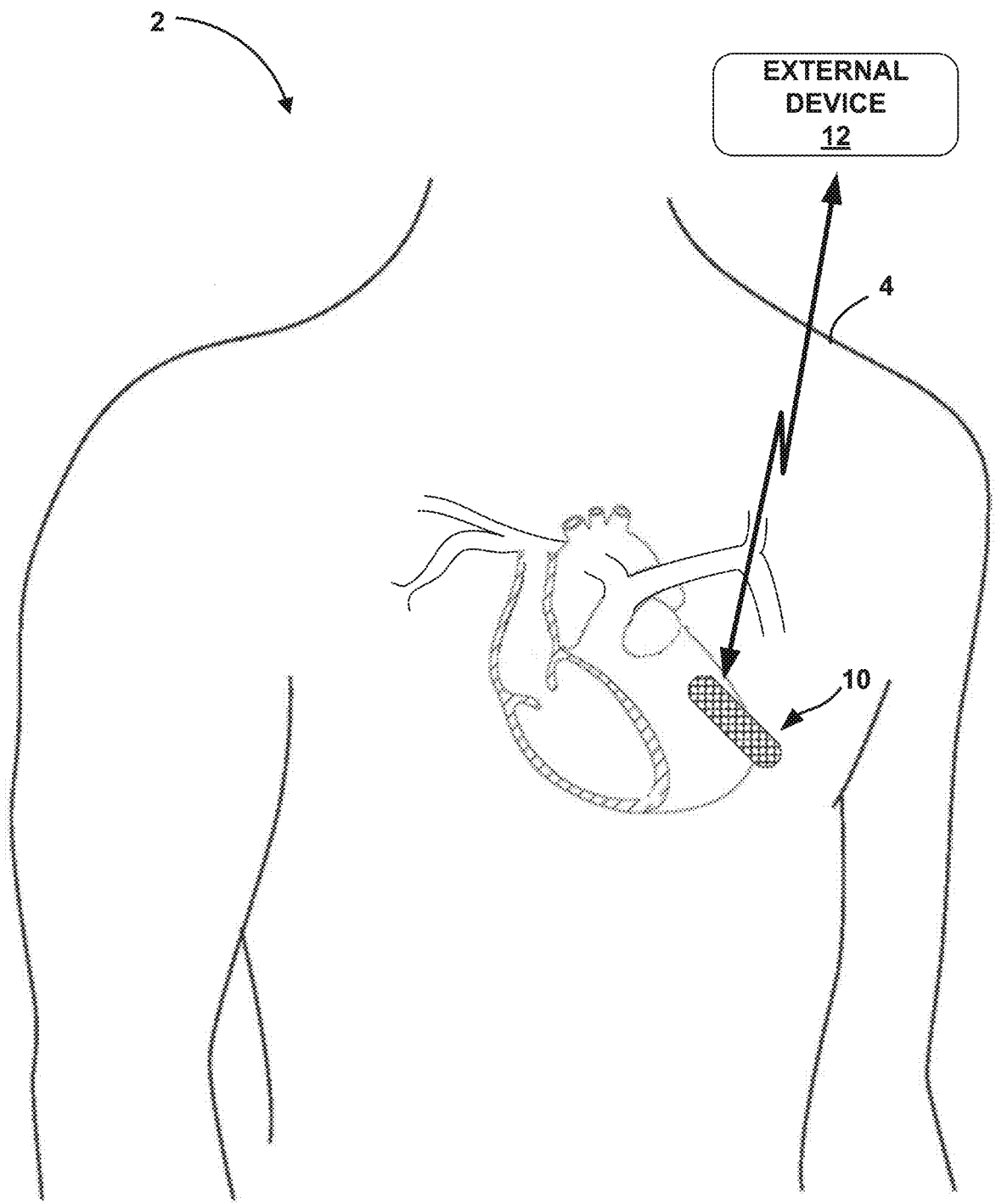
FIG. 1 illustrates the environment of an example medical system in conjunction with a patient.

FIG. 1 illustrates the environment of an example medical system 2 in conjunction with a patient 4, in accordance with one or more techniques of this disclosure. Patient 4 ordinarily, but not necessarily, will be a human. For example, patient 4 may be an animal needing ongoing monitoring for cardiac conditions. System 2 includes IMD 10. IMD 10 may include one or more electrodes (not shown) on a housing of IMD 10, or may be coupled to one or more leads that carry one or more electrodes. System 2 may also include external device 12.

The example techniques may be used with an IMD 10, which may be in wireless communication with at least one of external device 12 and other devices not pictured in FIG. 1. In some examples, IMD 10 may be implanted within patient 4. For example, IMD 10 may be implanted outside of a thoracic cavity of patient 4 (e.g., pectoral location illustrated in FIG. 1). In some examples, IMD 10 may be positioned near the sternum near or just below the level of the heart of patient 4, e.g., at least partially within the cardiac silhouette.

In some examples, IMD 10 may sense cardiac electrogram (EGM) signals via the plurality of electrodes and/or operate as a therapy delivery device. For example, IMD 10 may operate as a therapy delivery device to deliver electrical signals to the heart of patient 4, such as an implantable pacemaker, a cardioverter, and/or defibrillator, a drug delivery device that delivers therapeutic substances to patient 4 via one or more catheters, or as a combination therapy device that delivers both electrical signals and therapeutic substances.

In some examples, system 2 may include any suitable number of leads coupled to IMD 10, and each of the leads may extend to any location within or proximate to a heart or in the chest of patient 4. For example, other examples therapy systems may include three transvenous leads and an additional lead located within or proximate to a left atrium of a heart. As other examples, a therapy system may include a single lead that extends from IMD 10 into a right atrium or right ventricle, or two leads that extend into a respective one of a right ventricle and a right atrium.

In some examples, external device 12 may monitor temperature values received from IMD 10 according to the techniques described herein. For example, IMD 10 may obtain temperature data via one or more temperature sensing device(s) disposed within or otherwise fixed to IMD 10, such as fixed to the outer housing of IMD 10 or with temperature probes/leads entering into and/or extending out of IMD 10. For example, a temperature sensing device may be attached to the outer wall of IMD 10 with a temperature sensing lead wire inserted within IMD 10 and a temperature sensing lead wire extending outward from the temperature sensing device. In any event, IMD 10 may perform a data transfer of temperature data to one or more external devices 12. IMD 10 may perform the data transfer prior to or after processing the temperature data. For example, IMD 10 may transfer raw temperature data to external device 12 or in some instances, may transfer post-processing temperature data, such as smoothened temperature data that has been conditioned by a particular signal processing techniques (e.g., moving average or other low-pass filter, high-pass filter, band-pass filter, band-stop filter, etc.).

In some examples, IMD 10 takes the form of the Reveal LINQ™ Insertable Cardiac Monitor (ICM), or another ICM similar to, e.g., a version or modification of, the LINQ™ ICM, available from Medtronic plc. Such IMDs may facilitate relatively longer-term monitoring of patients during normal daily activities, and may periodically transmit collected data to a network service, such as the Medtronic CareLink® Network.

External device 12 may be a computing device with a display viewable by a user and an interface for providing input to external device 12 (i.e., a user input mechanism). The user may be a physician technician, surgeon, electrophysiologist, clinician, or patient 4. In some examples, external device 12 may be a notebook computer, tablet computer, computer workstation, one or more servers, cellular phone, personal digital assistant, handheld computing device, networked computing device, or another computing device that may run an application that enables the computing device to interact with IMD 10. For example, external device 12 may be a clinician, physician, or user programmer configured to communicate wirelessly with IMD 10 and perform data transfers between external device 12 and IMD 10. External device 12 is configured to communicate with IMD 10 and, optionally, another computing device (not illustrated in FIG. 1), via wired or wireless communication. External device 12, for example, may communicate via near-field communication (NFC) technologies (e.g., inductive coupling, NFC or other communication technologies operable at ranges less than 10-20 cm) and far-field communication technologies (e.g., Radio Frequency (RF) telemetry according to the 802.11 or Bluetooth® specification sets, or other communication technologies operable at ranges greater than near-field communication technologies). In some examples, external device 12 may include a programming head that may be placed proximate to the body of patient 4 near the IMD 10 implant site in order to improve the quality or security of communication between IMD 10 and external device 12. In some examples, external device 12 may be coupled to external electrodes, or to implanted electrodes via percutaneous leads.

The user interface of external device 12 may receive input from the user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. External device 12 can additionally or alternatively include a peripheral pointing device, such as a mouse, via which the user may interact with the user interface. In some examples, a display of external device 12 may include a touch screen display, and a user may interact with external device 12 via the display. It should be noted that the user may also interact with external device 12 remotely via a networked computing device.

In some examples, the user may use external device 12 to program or otherwise interface with IMD 10. External device 12 may be used to program aspects of sensing or data analysis performed by IMD 10 and/or therapies provided by IMD 10. In addition, external device 12 may be used to retrieve data from IMD 10. The retrieved data may include temperature values measured by IMD 10, infection indication data, and/or other physiological signals recorded by IMD 10. For example, external device 12 may retrieve information related to detection of a temperature shift detected by IMD 10, such as a rate of change that exceeds a predefined threshold. External device 12 may also retrieve cardiac EGM segments recorded by IMD 10, e.g., due to IMD 10 determining that an episode of arrhythmia or another malady occurred during the segment, or in response to a request to record the segment from patient 4 or another user. In other examples, the user may also use external device 12 to retrieve information from IMD 10 regarding other sensed physiological parameters of patient 4, such as activity or posture. As discussed in greater detail below with respect to FIG. 5, one or more remote computing devices may interact with IMD 10 in a manner similar to external device 12, e.g., to program IMD 10 and/or retrieve data from IMD 10, via a network.

Processing circuitry of medical system 2, e.g., of IMD 10, external device 12, and/or of one or more other computing devices, may be configured to perform the example techniques of this disclosure for measuring temperature to determine an infection indication. In some examples, the processing circuitry of medical system 2 analyzes temperature values sensed by IMD 10 to determine whether a change in temperature satisfies a predefined infection indication threshold.

Although described in the context of examples in which IMD 10 comprises an insertable or implantable IMD, example systems including one or more external devices of any type configured to sense temperature may be configured to implement the techniques of this disclosure. In some examples, IMD 10 or an external device 12 may use one or more of internal temperature and external temperature relative to IMD 10 in order to determine an infection status of patient 4, such as a device pocket infection. For example, external device 12 may receive signals indicative of external temperature, such as a core body temperature signal from IMD 10, and may receive signals indicative of an internal temperature of IMD 10, such as a device pocket temperature, and may use both temperature measurements to determine an infection status and identify a cause of the infection (e.g., a device pocket infection, bacterial infection of a body part, such as a bladder infection, etc.).

System 2 provides an alert to patient 4 and/or other users when an infection indication value indicates the onset of an infection event. The process for determining when to alert patient 4 involves comparing the infection indication value to one or more threshold values and is described in greater detail below. The alert may be an audible alert generated by IMD 10 and/or external device 12, a visual alert generated by external device 12, such as a text prompt or flashing buttons or screen, or a tactile alert generated by IMD 10 and/or external device 12 such as a vibration or vibrational pattern. Furthermore, the alert may be provided to other devices, e.g., via a network. Several different levels of alerts may be used based on the level of risk detected through the techniques described herein.

In examples in which IMD 10 also operates as a pacemaker, a cardioverter, and/or defibrillator, or otherwise monitors the electrical activity of the heart, IMD 10 may sense electrical signals attendant to the depolarization and repolarization of the heart of patient 4 via electrodes coupled to at least one lead. In some examples, IMD 10 can provide pacing pulses to the heart of patient 4 based on the electrical signals sensed within the heart of patient 4. IMD 10 may also provide defibrillation therapy and/or cardioversion therapy via electrodes located on at least one lead, as well as a housing electrode. IMD 10 may detect arrhythmia of the heart of patient 4, such as fibrillation of ventricles, and deliver defibrillation therapy to the heart of patient 4 in the form of electrical pulses.

Although described primarily in the context of examples in which IMD 10 is an insertable cardiac monitor, the techniques described herein may be implemented by medical device systems including any one or more implantable or external medical devices, such as any one or more monitors, pacemakers, cardioverters, defibrillators, heart assist devices, such as left-ventricular assist devices, neurostimulators, or drug delivery devices.

Figure 2:
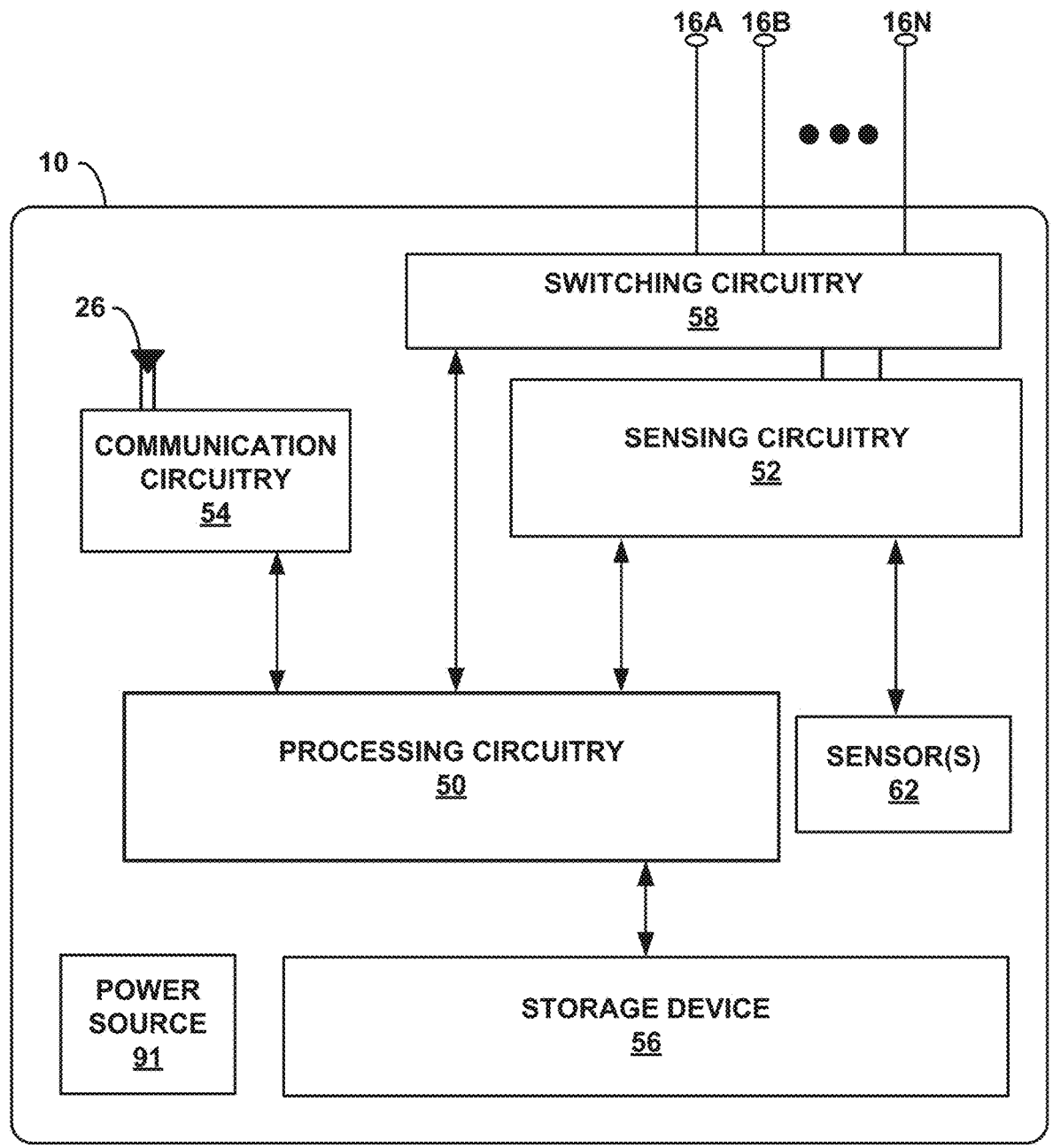
FIG. 2 is a functional block diagram illustrating an example configuration of an implantable medical device (IMD) of FIG. 1.

FIG. 2 is a functional block diagram illustrating an example configuration of IMD 10 of FIG. 1 in accordance with one or more techniques described herein. In the illustrated example, IMD 10 includes electrodes 16A-16N (collectively, "electrodes 16"), antenna 26, processing circuitry 50, sensing circuitry 52, communication circuitry 54, storage device 56, switching circuitry 58, sensor(s) 62, and power source 91.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may monitor signals from sensor(s) 62, which may include one or more temperature sensors, accelerometers, pressure sensors, and/or optical sensors, as examples. Sensor(s) 62 may include one or more temperature sensing devices. Any suitable sensor(s) 62 may be used to detect temperature or changes in temperature. In some examples, sensor(s) 62 may include a thermocouple, a thermistor, a junction-based thermal sensor, a thermopile, a fiber optic detector, an acoustic temperature sensor, a quartz or other resonant temperature sensor, a thermo-mechanical temperature sensor, a thin film resistive element, etc.

In some examples, sensing circuitry 52 may include one or more filters and amplifiers for filtering and amplifying signals received from sensor(s) 62 and/or electrodes 16. For example, sensing circuitry 52 may include one or more low-pass filters having various cutoff frequencies predefined to apply to temperature values obtained from sensor(s) 62, such as from one or more temperature sensors. In some examples, sensing circuitry 52 may include circuitry configured to digitally filter measured temperature values using one or more cutoff frequencies, or otherwise using one or more different filtering processes to achieve different degrees of smoothing of a series of temperature values. For example, sensing circuitry 52 may include certain processing circuitry, such as processing circuitry 50, configured to smooth temperature values determined over time to create smoothened temperature signals. In some examples, processing circuitry of sensing circuitry 52 may perform smoothing of temperature values measured by sensor(s) 62, such that processing circuitry 50 may perform various other techniques of this disclosure based on the smoothened temperature signals. In some examples, processing circuitry 50 may include sensing circuitry 52 with processing circuitry 50 being configured to smooth temperature values determined over time to create smoothened temperature signals (e.g., by performing digital and/or analog filtering).

In some examples, sensing circuitry 52 may be selectively coupled to electrodes 16 via switching circuitry 58 (e.g., to select the electrodes 16 and polarity) in order to sense impedance and/or cardiac signals. Sensing circuitry 52 may sense signals from electrodes 16, e.g., to produce a cardiac EGM or subcutaneous electrocardiogram (ECG), in order to facilitate monitoring electrical activity of the heart.

Processing circuitry 50 may cause sensing circuitry 52 to periodically measure a physiological parameters or other parameter values of IMD 10, such as temperature values. For temperature measurements, processing circuitry 50 may control sensing circuitry 52 to obtain a temperature measurement via one or more of sensor(s) 62.

Because either IMD 10 or external device 12 may be configured to include sensing circuitry 52, sensing circuitry may be implemented in one or more processors, such as processing circuitry 50 of IMD 10 or processing circuitry 80 of external device 12. Similar to processing circuitry 50, 80, 98 and other circuitry described herein, sensing circuitry 52 may be embodied as one or more hardware modules, software modules, firmware modules, or any combination thereof.

In some examples, processing circuitry 50 may receive temperature values of patient 4 from one or more other devices via communication circuitry 54. In some examples, the one or more other devices may include a sensor device, such as an activity sensor, heart rate sensor, a wearable device worn by patient 4, a temperature sensor, etc. That is, the one or more other devices may, in some examples, be external to IMD 10.

In some examples, processing circuitry 50 may receive temperature measurements from one or more of sensor(s) 62 via sensing circuitry 52. In another example, processing circuitry 50 may also receive temperature measurements from one or more other devices via communication circuitry 54.

In some examples, processing circuitry 50 may control the timing of temperature measurements based on a trigger. For examples, processing circuitry 50 may control sensing circuitry 52 and sensor(s) 62 based on a measurement trigger received via communication circuitry 54. In another example, processing circuitry 50 may transmit a request for data to one or more other devices via communication circuitry 54. For example, processing circuitry 50 may transmit a request to an external device requesting the external device provide physiological parameter data (e.g., heart rate, activity level, temperature values, etc.) to processing circuitry 50 via communication circuitry 54.

In some examples, the triggers might include activity level of patient 4, heart rate of patient 4, ambient temperature of surroundings of patient 4, etc. For example, processing circuitry 50 may control the timing of temperature measurements based on when the ambient temperature of patient 4 received from another device via communication circuitry 54 indicates that patient 4 is likely in a temperature controlled area (e.g., indoors). In another example, processing circuitry 50 may control the timing of temperature measurements based on when the ambient temperature or the surface temperature of patient 4 is within a predefined temperature range. In some examples, processing circuitry 50 may receive the trigger from another device via communication circuitry 54. In some instances, the trigger may be based on information processing circuitry 50 receives from another device via communication circuitry 54.

In a non-limiting example, processing circuitry 50 may receive signals indicating when patient 4 has low activity. In response to receiving the signal indicating an activity level, processing circuitry 50 may control sensing circuitry 52 to measure one or more temperature values using one of sensor(s) 62. In another example, processing circuitry 50 may receive signals indicating when patient 4 has lower or higher heart rate compared to that of a heart rate threshold or signals indicating when patient 4 has a temperature that has become too low or too high compared to that of certain temperature thresholds, etc. In such examples, processing circuitry 50 may determine heart rate values of patient 4 based on signals from sensing circuitry 52 regarding activity of the heart sensed via electrodes, such as electrodes 16. In any event, processing circuitry 50 may determine whether the received signals include triggering information that communicate to sensing circuitry 52 that sensing circuitry 52 is to perform physiological parameter measurements (e.g., temperature measurements) using one of sensor(s) 62.

In some examples, processing circuitry 50 may determine whether a combination of one or more signals received from one or more transmitting devices contains triggering information. Processing circuitry 50 may determine one or more signals individually include triggering information. In some examples, processing circuitry 50 may determine one or more signals in combination include triggering information. In response to determining the occurrence of triggering information, processing circuitry 50 may cause sensing circuitry 52 to measure one or more temperature values using one of sensor(s) 62. In some examples, processing circuitry 50 may additionally use timing information. For example, processing circuitry 50 may start a timer based on the triggering information. In some examples, processing circuitry 50 may cause sensing circuitry 52 to measure temperature values in accordance with a timing constraint (e.g., only perform measurements at night) following a triggering event, regardless of when the triggering event occurred during the day.

In some examples, processing circuitry 50 may control the measurement of temperature values on a periodic basis, such as on an hourly basis, daily basis, weekly basis, or the like. In one example, sensing circuitry 52 may measure temperature values during a particular portion of a day. As an example, sensing circuitry 52 may measure temperature values every twenty minutes for a predetermined number of hours, such as between noon and 5 pm. Processing circuitry 50 may determine a final measured temperature value by calculating an average of the measurements. In this case, the daily value may be the average of the temperature values measured by sensing circuitry 52 during the day (e.g., within a 24-hr time period, within a 24-hr time period where measurements are selectively taken between particular times and/or in response to certain triggers, etc.).

In some examples, sensing circuitry 52 may be configured to sample temperature measurements at a particular sampling rate. In such examples, sensing circuitry 52 may be configured to perform downsampling of the received temperature measurements. For example, sensing circuitry 52 may perform downsampling in order to decrease the throughput rate for processing circuitry 50. This may be particularly advantageous where sensing circuitry 52 has a high sampling rate when active.

As used herein, the term "temperature value" is used in a broad sense to indicate any collected, measured, and/or calculated value. In some examples, temperature values are derived from temperature signals received from one or more of sensor(s) 62. For example, temperature values may include an average (e.g., mean, mode, standard deviation) of temperature signals received from one or more of sensor(s) 62.

In the example illustrated in FIG. 2, processing circuitry 50 is capable of performing the various techniques described with reference to FIGS. 6-16. To avoid confusion, processing circuitry 50 is described as performing the various temperature processing techniques proscribed to IMD 10, but it should be understood that these techniques may also be performed by other processing circuitry (e.g., processing circuitry 80 of external device 12, etc.).

In various examples, processing circuitry 50 may perform one, all, or any combination of the plurality of infection indication techniques discussed in greater detail below. In performing the infection indication techniques, IMD 10 may generate an alert upon determining that an increase in an infection indication value indicates that patient 4 is likely to have an infection, such as a device pocket infection. For example, IMD 10 may provide an audible or tactile alert in the form of a beeping noise or a vibrational pattern. Alternatively, IMD 10 may send an alert signal to external device 12 that causes external device 12 to provide an alert to patient 4. External device 12 may provide an audible, visual, or tactile alert to patient 4. Once patient 4 is alerted, patient 4 may then seek medical attention, e.g., by checking into a hospital or clinic. The alerts may be separated into various degrees of seriousness as indicated by the infection indication value.

Sensing circuitry 52 may also provide one or more temperature values to processing circuitry 50 for analysis, e.g., for analysis to identify a possible infection according to the techniques of this disclosure. In some examples, processing circuitry 50 may store the temperature values to storage device 56. Processing circuitry 50 of IMD 10, and/or processing circuitry of another device that retrieves data from IMD 10, may analyze the temperature values to identify infection conditions according to the techniques of this disclosure.

Communication circuitry 54 may include any suitable hardware, firmware, software or any combination thereof for communicating with another device, such as external device 12, another networked computing device, or another IMD or sensor. Under the control of processing circuitry 50, communication circuitry 54 may receive downlink telemetry from, as well as send uplink telemetry to external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network. Antenna 26 and communication circuitry 54 may be configured to transmit and/or receive signals via inductive coupling, electromagnetic coupling, near-field communications, RF communication, Bluetooth®, WI-FI™, or other proprietary or non-proprietary wireless communication schemes. For example, processing circuitry 50 may provide data to be uplinked to external device 12 via communication circuitry 54 and control signals using an address/data bus. In some examples, communication circuitry 54 may provide received data to processing circuitry 50 via a multiplexer.

In other example, processing circuitry 50 may send temperature data to external device 12 via communication circuitry 54. For example, IMD 10 may send external device 12 collected temperature measurements, which are then analyzed by external device 12. In such examples, external device 12 performs the processing techniques described herein. Alternatively, IMD 10 may perform the processing techniques and transmit the processed temperature data and/or indications of whether infection is detected to external device 12 for reporting purposes, e.g., for providing an alert to patient 4 or another user.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media. For example, storage device 56 may include random access memory (RAM), read-only memory (ROM), non-volatile RAM (NVRAM), electrically-erasable programmable ROM (EEPROM), erasable programmable ROM (EPROM), flash memory, or any other digital media. Storage device 56 may store, as examples, programmed values for one or more operational parameters of IMD 10 and/or data collected by IMD 10 for transmission to another device using communication circuitry 54. Data stored by storage device 56 and transmitted by communication circuitry 54 to one or more other devices may include temperature values.

The various components of IMD 10 are coupled to power source 91, which may include a rechargeable or non-rechargeable battery. A non-rechargeable battery may be capable of holding a charge for several years, while a rechargeable battery may be inductively charged from an external device, such as external device 12, on a daily, weekly, or annual basis, for example.

Figure 3:
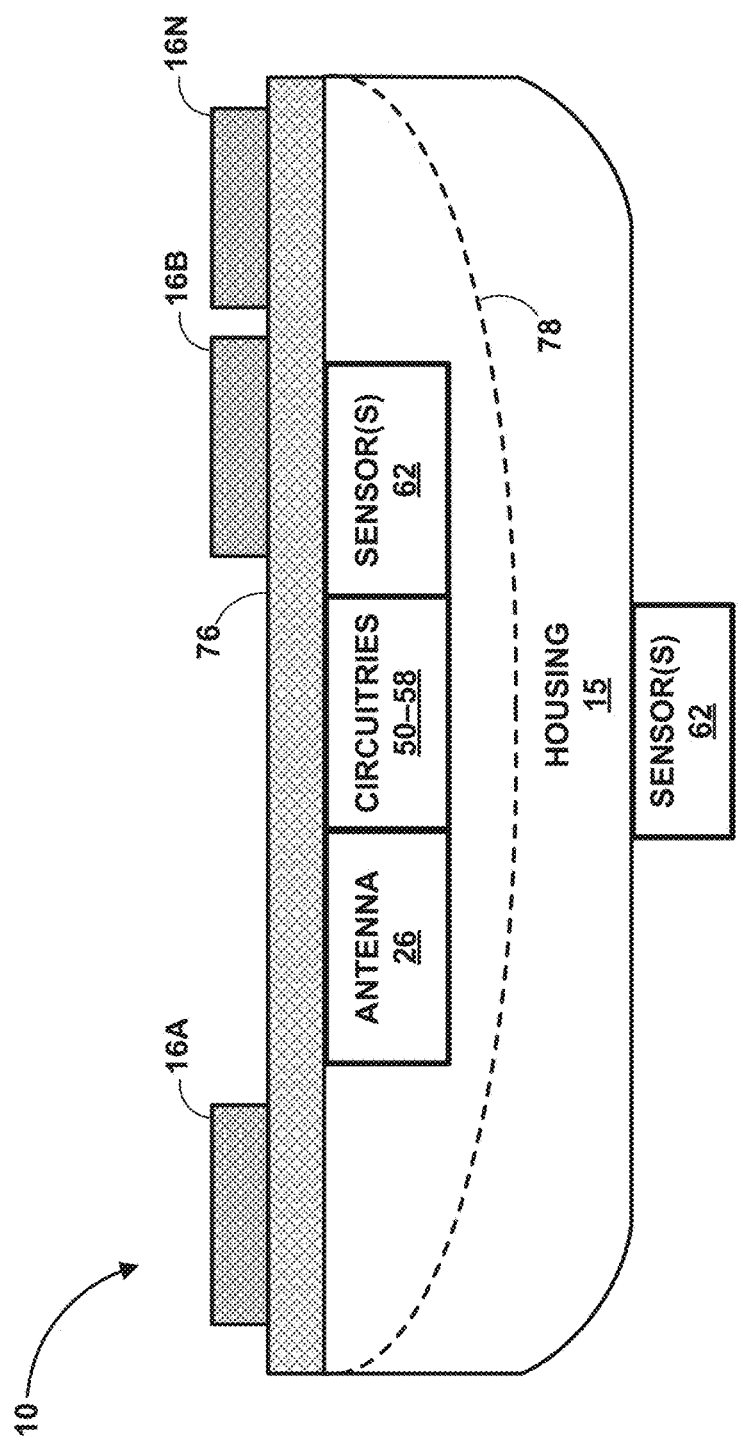
FIG. 3 is a conceptual side-view diagram illustrating an example IMD of a medical system of FIGS. 1 and/or 2 in greater detail.

FIG. 3 is a conceptual side-view diagram illustrating an example configuration of IMD 10 of FIG. 1. In the example shown in FIG. 3, IMD 10 may include a leadless device having a housing 15 and an insulative cover 76. Electrodes 16 may be formed or placed on an outer surface of cover 76. Circuitries 50-58 and/or sensor(s) 62, described above with respect to FIG. 2, may be formed or placed on an inner surface of cover 76, or otherwise within housing 15. Sensor(s) 62 may include one or more temperature sensing devices fixed to an outer housing 15 of IMD 10 or insulative cover 76, instead of or in addition to temperatures sensors within housing 15. In a non-limiting example, IMD 10 may include more than two temperature sensing devices on the inside of IMD 10 and in addition, may include more than two temperature sensing device on the outside of IMD 10. In some examples, temperature data obtained from multiple temperature sensing device may be averaged or otherwise combined to obtain a representative temperature signal that may also be smoothed as discussed with reference to FIG. 6.

In the illustrated example, antenna 26 is formed or placed on the inner surface of cover 76, but may be formed or placed on the outer surface in some examples. In some examples, one or more of sensor(s) 62 may be formed or placed on the outer surface of cover 76. In some examples, insulative cover 76 may be positioned over housing 15, such that housing 15 and insulative cover 76 enclose antenna 26, sensor(s) 62, and/or circuitries 50-62, and protect the antenna, sensor(s), and circuitries from fluids.

One or more of antenna 26, sensor(s) 62, and/or circuitries 50-58 may be formed on the inner side of insulative cover 76, such as by using flip-chip technology. Insulative cover 76 may be flipped onto a housing 15. When flipped and placed onto housing 15, the components of IMD 10 formed on the inner side of insulative cover 76 may be positioned in a gap 78 defined by housing 15. Electrodes 16 may be electrically connected to switching circuitry 58 through one or more vias (not shown) formed through insulative cover 76. Insulative cover 76 may be formed of sapphire (i.e., corundum), glass, parylene, and/or any other suitable insulating material. Housing 15 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

In a non-limiting example, one or more temperature sensing devices, may be formed or placed on the outer surface of housing 15 or insulative cover 76, with additional sensor(s) 62, such as one or more additional temperature sensing devices, may be formed within housing 15, such as on a printed circuit board (PCB) disposed within housing 15. In some examples, a temperature sensing device may be formed or placed on the outer surface of housing 15 or insulative cover 76 using a connection interface. The connection interface, in some instances, may include a wired connection interface. For example, a temperature sensing device may be placed on the outer surface of housing 15 or insulative cover 76 using a press-fit connector, solder paste, conductive mounting pins, input-output cables or other wire connectors, threaded connectors, wire pads, press-in pins, etc., or various combinations thereof. In an example involving a wireless connection interface, the temperature sensing device may include communication and processing circuitry to transmit temperate values to one or more other devices, such as to communication circuitry 54, communication circuitry 82 or otherwise over network 92. In one illustrative example, sensor(s) 62 on an outer surface of cover 76 may be connected to circuitry within housing 15 through one or more vias (not shown) formed through insulative cover 76.

Figure 4:
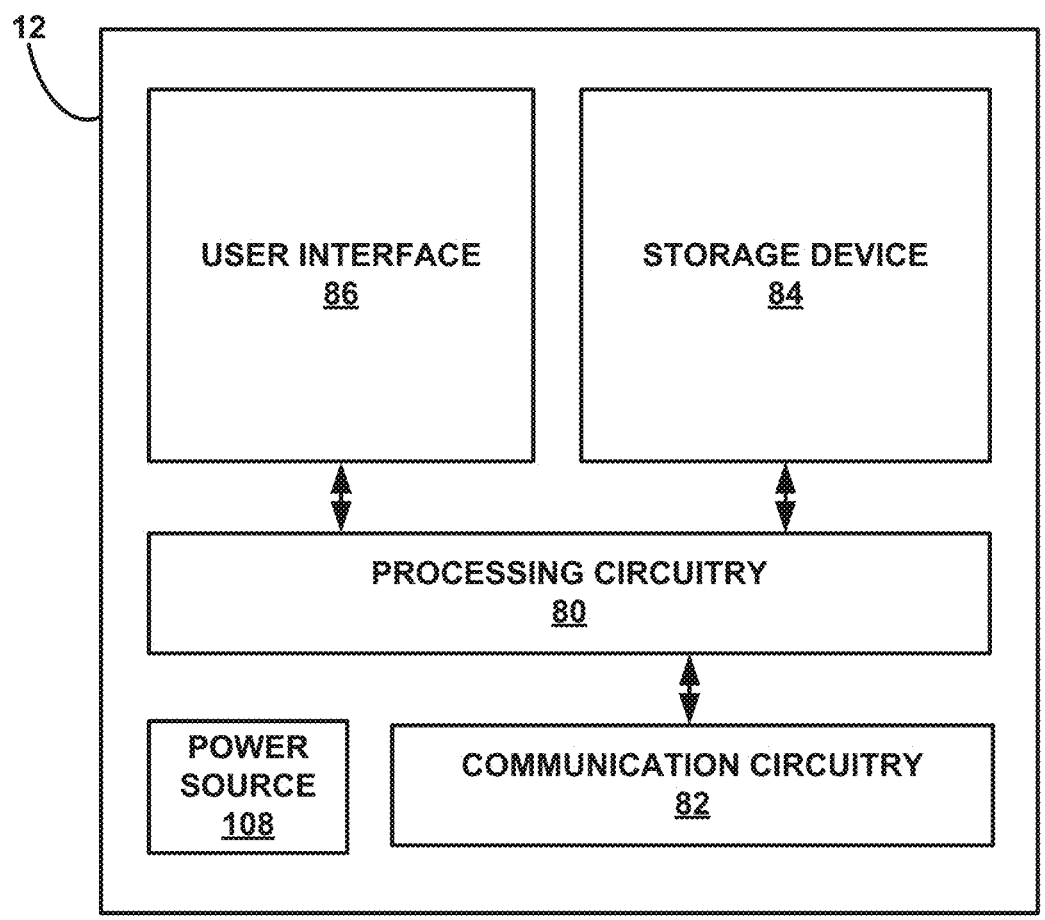
FIG. 4 is a functional block diagram illustrating an example configuration of the external device of FIG. 1.

FIG. 4 is a block diagram illustrating an example configuration of components of external device 12. In the example of FIG. 4, external device 12 includes processing circuitry 80, communication circuitry 82, storage device 84, and user interface 86.

Processing circuitry 80 may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device. Communication circuitry 82 may be configured to transmit or receive signals via inductive coupling, electromagnetic coupling, Near Field Communication (NFC), RF communication, Bluetooth®, WI-FI™, or other proprietary or non-proprietary wireless communication schemes. Communication circuitry 82 may also be configured to communicate with devices other than IMD 10 via any of a variety of forms of wired and/or wireless communication and/or network protocols.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution. Storage device 84 may also store historical temperature data, current temperature data, etc.

Data exchanged between external device 12 and IMD 10 may include operational parameters (e.g., resolution parameters regarding the resolution of temperature measurements, such as a sampling rate). External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., temperature data) to external device 12. In turn, external device 12 may receive the collected data from IMD 10 and store the collected data in storage device 84. Processing circuitry 80 may implement any of the techniques described herein to analyze temperature values received from IMD 10, e.g., to determine infection indications. Using the temperature analysis techniques disclosed herein, processing circuitry 80 may determine an infection status of patient 4 and/or generate an alert based on the infection status.

A user, such as a clinician or patient 4, may interact with external device 12 through user interface 86. User interface 86 includes a display (not shown), such as a liquid crystal display (LCD) or a light emitting diode (LED) display or other type of screen, with which processing circuitry 80 may present information related to IMD 10, e.g., cardiac EGMs, indications of detections of temperature changes, and quantifications of temperature changes. In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to the user, receiving voice commands from the user, or both.

Power source 108 delivers operating power to the components of external device 12. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within external device 12. In other embodiments, traditional batteries (e.g., nickel cadmium or lithium ion batteries) may be used. In addition, external device 12 may be directly coupled to an alternating current outlet to power external device 12. Power source 108 may include circuitry to monitor power remaining within a battery. In this manner, user interface 86 may provide a current battery level indicator or low battery level indicator when the battery needs to be replaced or recharged. In some cases, power source 108 may be capable of estimating the remaining time of operation using the current battery.

Figure 5:
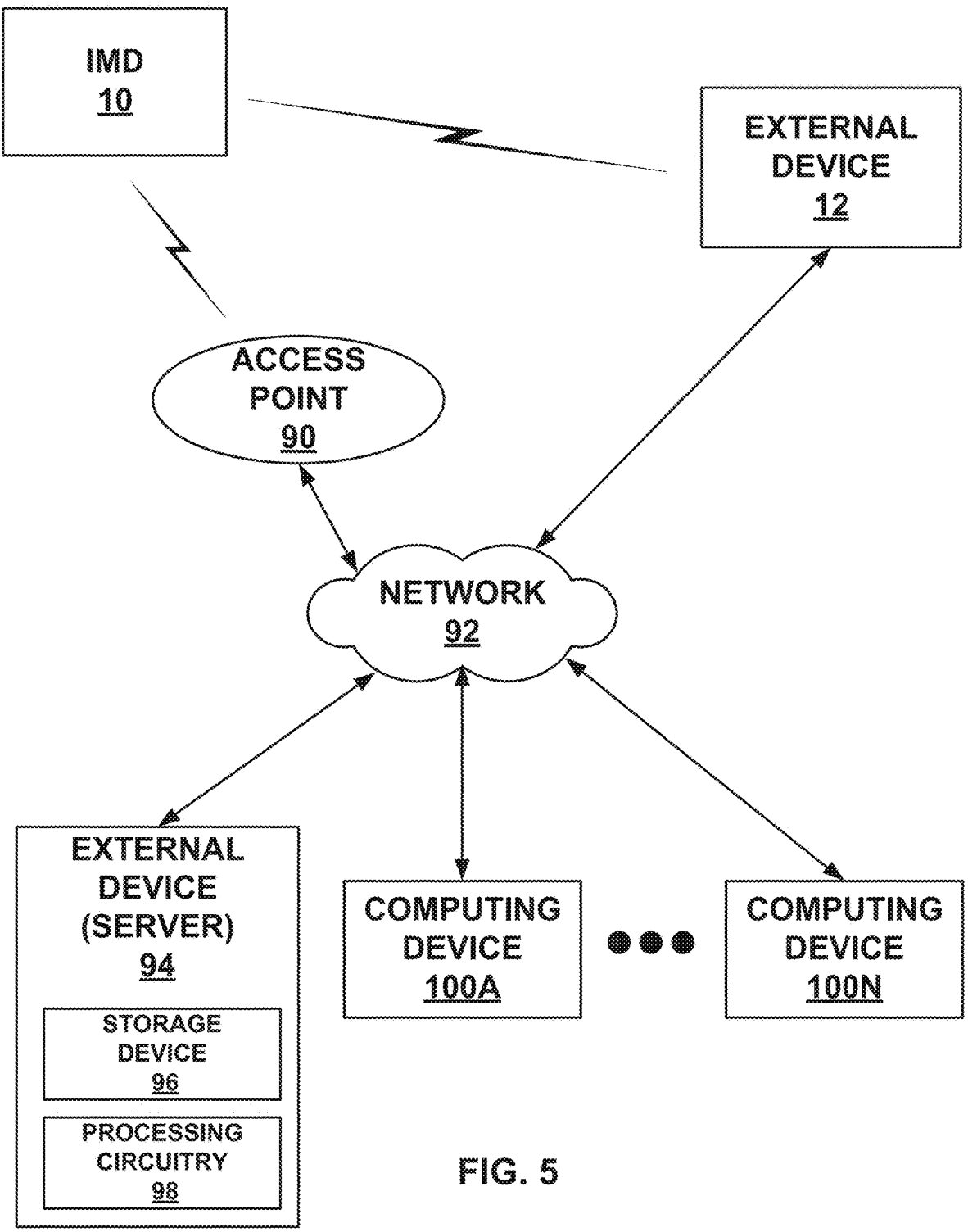
FIG. 5 is a block diagram illustrating an example system that includes an access point, a network, external computing devices, such as a server, and one or more other computing devices, which may be coupled to the IMD and external devices of FIGS. 1-4.

FIG. 5 is a block diagram illustrating an example system that includes an access point 90, a network 92, external computing devices, such as a server 94, and one or more other computing devices 100A-100N (collectively, "computing devices 100"), which may be coupled to IMD 10 and external device 12 via network 92, in accordance with one or more techniques described herein. In this example, IMD 10 may use communication circuitry 54 to communicate with external device 12 via a first wireless connection, and to communicate with an access point 90 via a second wireless connection. In the example of FIG. 5, access point 90, external device 12, server 94, and computing devices 100 are interconnected and may communicate with each other through network 92. Network 92 may comprise a local area network, wide area network, or global network, such as the Internet. The system of FIG. 5 may be implemented, in some aspects, with general network technology and functionality similar to that provided by the Medtronic CareLink® Network.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. IMD 10 may be configured to transmit data, such as temperature values, infection indication values, and/or cardiac electrograms (EGMs), to access point 90. Access point 90 may then communicate the retrieved data to server 94 via network 92.

In some cases, server 94 may be configured to provide a secure storage site for data that has been collected from IMD 10 and/or external device 12. In some cases, server 94 may assemble data in web pages or other documents for viewing by trained professionals, such as clinicians, via computing devices 100. One or more aspects of the illustrated system of FIG. 5 may be implemented with general network technology and functionality, which may be similar to that provided by the Medtronic CareLink® Network.

In some examples, server 94 may monitor IMD temperature, e.g., based on measured temperature information received from IMD 10 and/or external device 12 via network 92, to identify an infection status of patient 4 using any of the techniques described herein. Server 94 may provide alerts relating to an infection status of patient 4 via network 92 to patient 4 via access point 90, or to one or more clinicians via computing devices 100. In examples such as those described above in which IMD 10 and/or external device 12 monitor the temperature, server 94 may receive an alert from IMD 10 or external device 12 via network 92, and provide alerts to one or more clinicians via computing devices 100. In some examples, server 94 may generate web-pages to provide alerts and information regarding the infection status of patient 4, and may comprise a memory to store alerts and diagnostic or physiological parameter information for a plurality of patients.

In some examples, one or more of computing devices 100 may be a tablet or other smart device located with a clinician, by which the clinician may program, receive alerts from, and/or interrogate IMD 10. For example, the clinician may access data collected by IMD 10 through a computing device 100, such as when patient 4 is in between clinician visits, to check on a status of a medical condition. In some examples, the clinician may enter instructions for a medical intervention for patient 4 into an application executed by computing device 100, such as based on a status of a patient condition determined by IMD 10, external device 12, server 94, or any combination thereof, or based on other patient data known to the clinician. Device 100 then may transmit the instructions for medical intervention to another of computing devices 100 located with patient 4 or a caregiver of patient 4. For example, such instructions for medical intervention may include an instruction to change a drug dosage, timing, or selection, to schedule a visit with the clinician, or to seek medical attention. In further examples, a computing device 100 may generate an alert to patient 4 based on a status of a medical condition of patient 4, which may enable patient 4 proactively to seek medical attention prior to receiving instructions for a medical intervention. In this manner, patient 4 may be empowered to take action, as needed, to address his or her medical status, which may help improve clinical outcomes for patient 4.

In the example illustrated by FIG. 5, server 94 includes a storage device 96, e.g., to store data retrieved from IMD 10, and processing circuitry 98. Although not illustrated in FIG. 5 computing devices 100 may similarly include a storage device and processing circuitry. Processing circuitry 98 may include one or more processors that are configured to implement functionality and/or process instructions for execution within server 94. For example, processing circuitry 98 may be capable of processing instructions stored in storage device 96 (e.g., stored in memory). Processing circuitry 98 may include, for example, microprocessors, DSPs, ASICs, FPGAs, or equivalent discrete or integrated logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98. Processing circuitry 98 of server 94 and/or the processing circuitry of computing devices 100 may implement any of the techniques described herein to analyze temperature values received from IMD 10, e.g., to determine an infection status of patient 4 (e.g., a device pocket infection).

Storage device 96 may include a computer-readable storage medium or computer-readable storage device. In some examples, storage device 96 includes one or more of a short-term memory or a long-term memory. Storage device 96 may include, for example, RAM, DRAM, SRAM, magnetic discs, optical discs, flash memories, or forms of EPROM or EEPROM. In some examples, storage device 96 is used to store data indicative of instructions for execution by processing circuitry 98.

Figure 6:
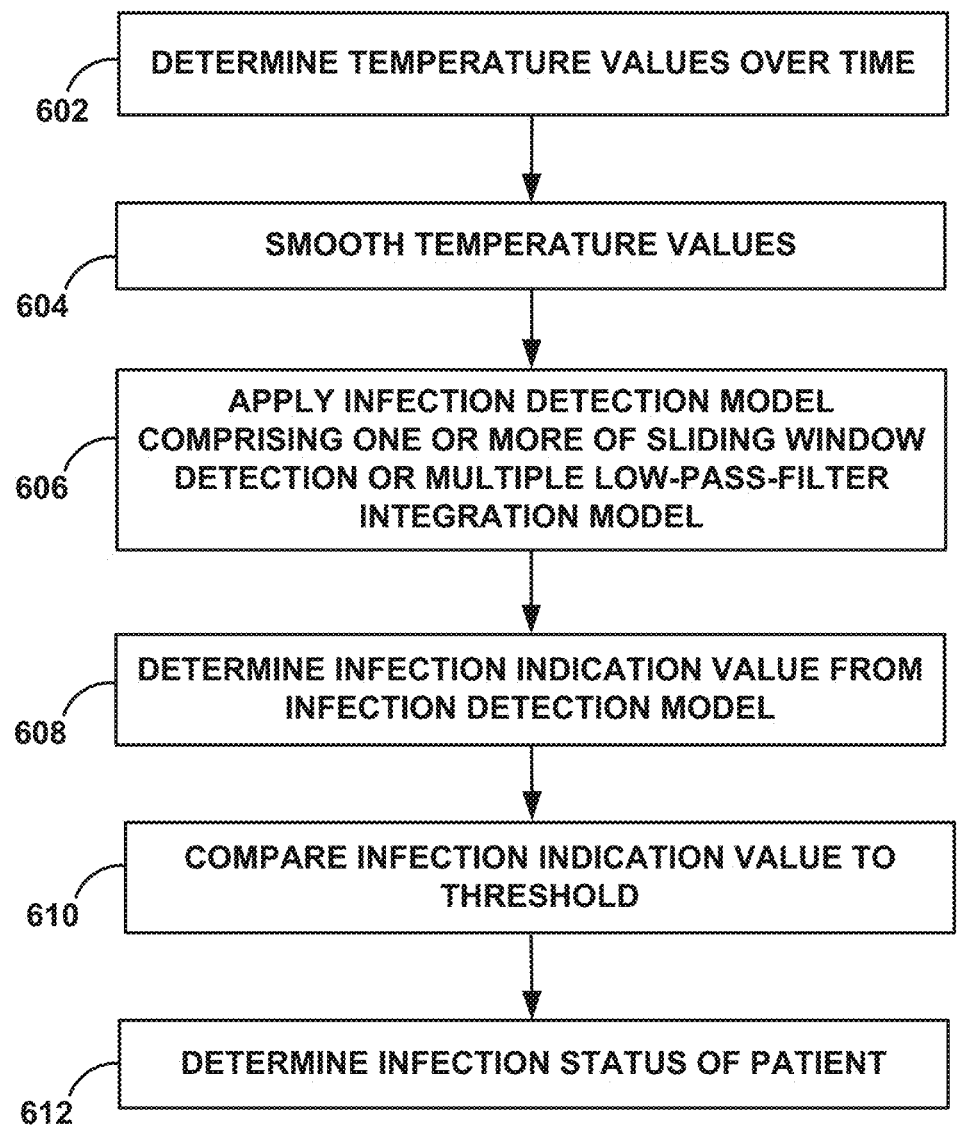
FIG. 6 is a flow diagram illustrating an example operation for determining an infection status of a patient, in accordance with one or more techniques disclosed herein.

FIG. 6 is a flow diagram illustrating an example operation for identifying an infection status of a patient, in accordance with one or more techniques of this disclosure. Although described as being performed by IMD 10, the example method of FIG. 6 may be performed by any one or more of IMD 10, external device 12, or server 94, e.g., by the processing circuitry or sensing circuitry of any one or more of these devices. For example, IMD 10 may transmit temperature values or other temperature data to external device 12 and/or server 94, with external device 12 and/or server 94 performing various other techniques of this disclosure.

In some examples, processing circuitry, e.g., processing circuitry 50 of IMD 10, processing circuitry 80 of external device 12, or processing circuitry 98 of server 94, or sensing circuitry 52, may determine temperature values over time based on temperature signals (602). For example, processing circuitry 50 may obtain raw temperature data from one or more of sensor(s) 62. For example, sensor(s) 62 may include one or more temperature sensing devices disposed within or located adjacent IMD 10. Sensor(s) 62 may detect temperature in and/or around IMD 10. In another example, processing circuitry 80 of external device 12 or processing circuitry 98 of server 94 may receive temperature values from IMD 10.

Figure 7:
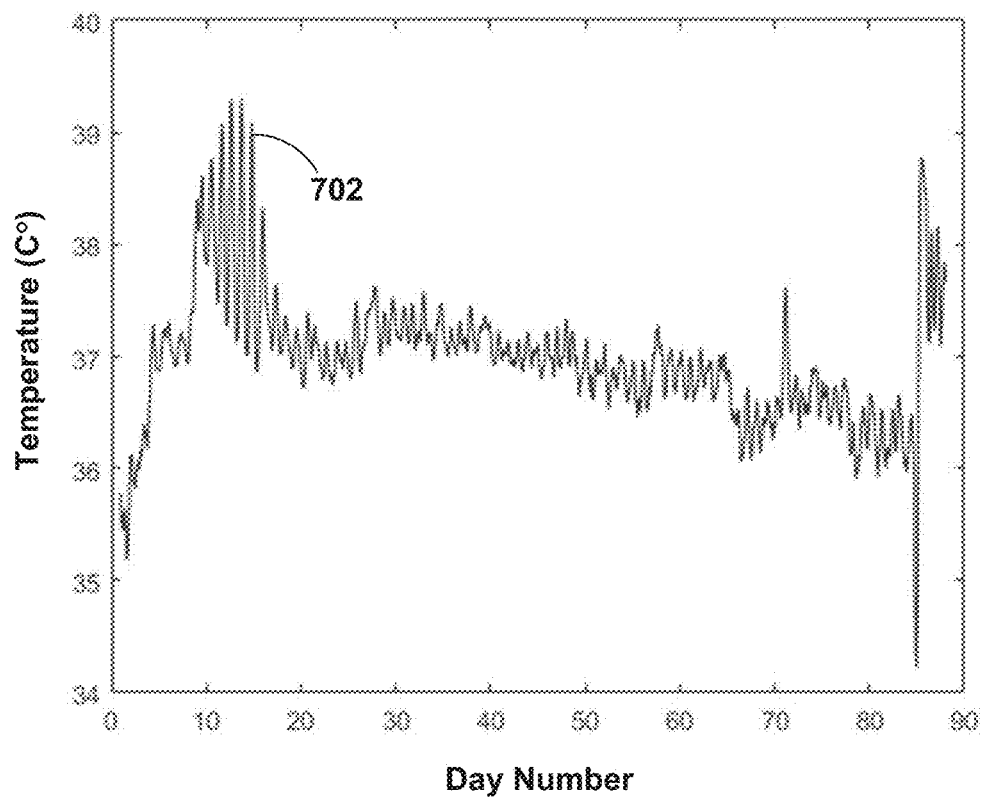
FIG. 7 is a conceptual graph illustrating raw temperature data collected from a temperature sensing device coupled to an IMD, collected in accordance with one or more techniques disclosed herein.

In some instances, a temperature sensing device of sensor(s) 62 may sense temperature values that include increases or decreases in temperature of IMD 10. FIG. 7 provides an example illustration of a graph showing increases and decreases in temperature obtained from a temperature sensing device of IMD 10. FIG. 7 illustrates temperature data that may be obtained over time from one of sensor(s) 62 configured as a temperature sensing device. A person of skill in the art will understand that temperature values may be obtained so as to include any temperature unit, including Celsius (C°), Fahrenheit (F°), etc., and may be converted therebetween units depending on particular implementations. While the x-axis of FIG. 7 shows "Day Number," as an example x-axis unit, the techniques of this disclosure are not so limited, and the temperature values may be collected at any rate or periodicity. In some examples, sensing circuitry 52 may obtain temperature values from sensor(s) 62 every second, every minute, hourly, daily, etc. or may obtain temperature values from sensor(s) 62 in an aperiodic fashion. For example, sensing circuitry 52 may obtain temperature values over time in response to a triggering event, such as in response to an incoming temperature request signal from external device 12 or may perform random temperature measurements at random times during a set time period (e.g., randomly throughout each day). In some examples, sensing circuitry 52 may determine temperature values based on a sampling rate of one of temperature sensing devices of sensor(s) 62. In some examples, the temperature values obtained over time may be obtained on a daily basis as shown in FIG. 7. In some instances, the temperature values obtained over time may be obtained on any periodic or aperiodic basis or combinations thereof.

Processing circuitry 50 may determine temperature values of IMD 10 over time as a series of discrete temperature values. In some examples, processing circuitry 50 may determine the temperature values at a sampling rate during each of a plurality of sampling periods during a predefined time period. For example, processing circuitry 50 may determine temperature values at a sampling rate of twice every hour over the course of a 24-hour time period. In another example, processing circuitry 50 may determine temperature values at a sampling rate of once every hour during specific times of the day, such as between 11:00 pm and 6:00 am or between 7:00 am and 5:00 pm. In some examples, processing circuitry 50 may determine temperature values at a sampling rate of once per minute.

In some examples, processing circuitry 50 may determine sampling rate parameters based on input received from a user specifying such parameters. For example, processing circuitry 50 may receive, from external device 12, sampling rate parameters provided by a user via user interface 86. In any case, processing circuitry 50 may smoothen temperature values determined over time using various filtering techniques (e.g., moving average filters, digital filters, low pass differentiator filters, etc.). For example, processing circuitry 50 may determine an average of the discrete temperature values measured at the particular sampling rate in order to determine an average of the temperature values over time. In some examples, the average may include a series of averages, such as a moving average of the temperature values, low-pass filtered data, or other smoothing methods discussed herein.

It should be noted that a person of skill in the art will understand that the illustrative graphs referenced herein, such as the graph shown in FIGS. 7, 8, 11, and 13, may be embodied in other forms, such as tables of data. For example, processing circuitry, e.g., processing circuitry 50 of IMD 10, processing circuitry 80 of external device 12, or processing circuitry 98 of server 94, may store temperature values and/or smoothened temperature signals in a database (e.g., of storage device 56, storage device 84, or storage device 96). A database may include any data structure (and/or combinations of multiple data structures) for storing and/or organizing data, including, but not limited to, relational databases (e.g., Oracle databases, MySQL databases, etc.), non-relational databases (e.g., NoSQL databases, etc.), in-memory databases, spreadsheets, as comma separated values (CSV) files, extensible markup language (XML) files, TeXT (TXT) files, flat files, spreadsheet files, and/or any other widely used or proprietary format for data storage. For example, the smoothened temperature signals may be laid out as individual, structured XML segments. That is, while FIGS. 7, 8, 11, and 13 are illustrated as graphical representations of temperature values over time, the techniques of this disclosure are not so limited, and processing circuitry, e.g., processing circuitry 50, may process or store temperature values in other forms.

Figure 8:
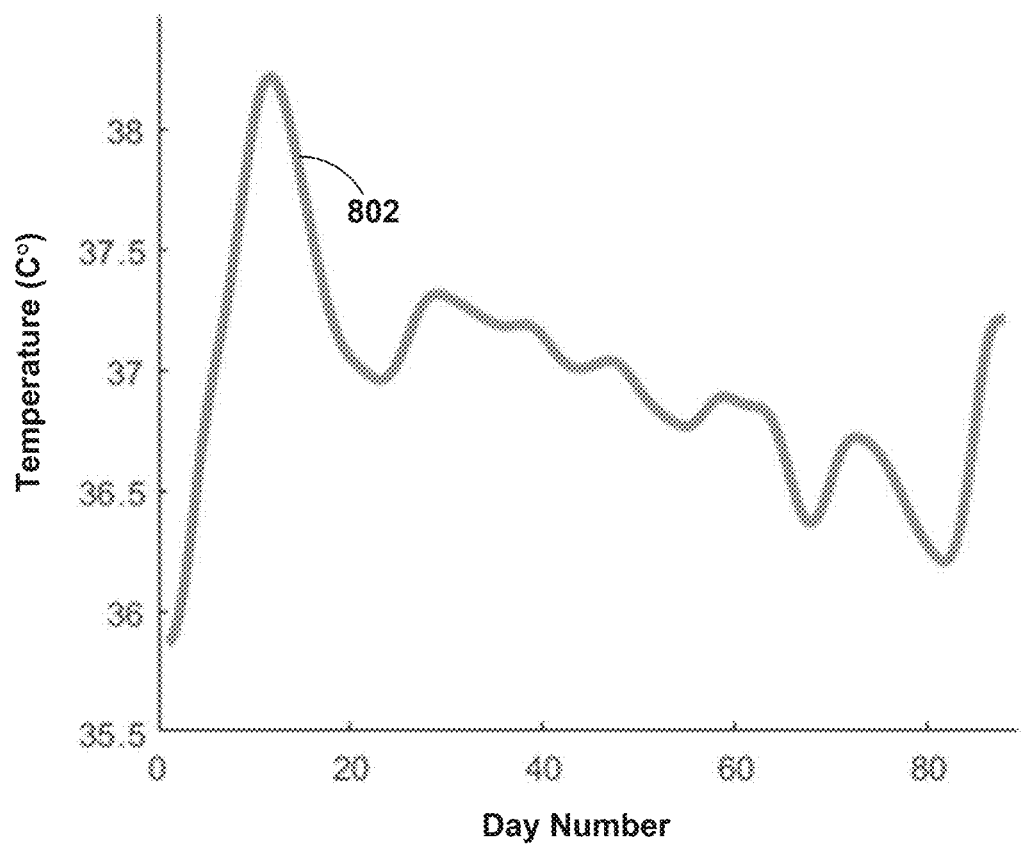
FIG. 8 is a conceptual graph illustrating smoothened temperature data, smoothened in accordance with one or more techniques disclosed herein.

In some examples, processing circuitry, e.g., processing circuitry 50 of IMD 10, processing circuitry 80 of external device 12, or processing circuitry 98 of server 94, or sensing circuitry 52, may smooth the temperature values determined over time to create a smoothened temperature signal (604). FIG. 8 provides an example illustration of a graph showing a smoothened signal 802 based on temperature values 702 obtained from one of sensor(s) 62. Smoothened signal 802 of FIG. 8 represents changes over time with respect to the temperature values 702. The smoothened signal may be smoothened so as to decrease an amount of noise in temperature values 702 caused by various factors, including environmental factors, diurnal variations, etc. For example, a particular detection model may be more sensitive to temperature changes during parts of the day where temperatures of a body naturally increase, but where an infection may not actually be present. In addition, diurnal variations may be attributable to an amount of physical activity of patient 4, certain attire worn by patient 4 that increase the temperature of patient 4, etc. In any event, processing circuitry 50 may perform more accurately to detect device pocket infections when the signal is smoothened using various smoothing methods, including the application of a low pass filter or determination of a moving average (e.g., a Low Pass Finite Impulse Response (FIR) filter, etc.).

In one example, processing circuitry, e.g., processing circuitry 50 of IMD 10, processing circuitry 80 of external device 12, or processing circuitry 98 of server 94, or sensing circuitry 52, may apply a low pass filter to the plurality of temperature values to determine the smoothened signal. For example, processing circuitry 50 may smoothen the temperature values using a digital filter or in some instances, an analog filter. In one example, processing circuitry 50 may apply a digital filter that increases signal-to-noise ratio (SNR) to create a smoothened temperature signal by filtering out high frequency noise or other high frequency variations from temperature values determined over time. In another example, processing circuitry 50 may smoothen the temperature values using a low pass differentiator filter that performs smoothing based on predefined coefficients and/or smoothing differentiator filter functions to remove high frequency variations in temperature values determined over time.

In some examples, processing circuitry 50 may apply a low pass filter that passes low-frequency temperature variations while impeding high-frequency temperature variations. The low pass filter may have a predefined cutoff frequency that attenuates temperature variations exceeding that of the cutoff frequency. In this way, processing circuitry 50 may apply the filter so as to filter, smooth, or otherwise take into account normal daily variations in temperature values. In some examples, a low pass filter, such as a moving average filter, or other smoothing filter, may be applied to remove normal variations that occur in temperature on a day-to-day basis. For example, in any given day, temperature values may increase during parts of the day when the ambient temperature is increasing or when a person is active and decrease during parts of the day when the ambient temperature is decreasing.

In an illustrative example, processing circuitry 50 may record temperature data at a particular rate. For example, processing circuitry 50 may record temperature data at 1 sample/minute. In addition, processing circuitry 50 may sample the temperature data at a particular sampling rate, such as at X times per day sampling rate. For example, processing circuitry 50 may sample the temperature data at a 1 sample/360 minutes (e.g., 4 times per day). In any case, processing circuitry 50 may set the cutoff frequency for the low pass filter set at a particular nominal value. For example, processing circuitry 50 may set the cutoff frequency at 1/10,000 minute or approximately 7 days. In some instances, the cutoff frequency value may be predefined, such as by a user. Further, the low pass filter may be a type of butterworth filter. In a non-limiting example, the low pass filter may be a sixth order butterworth low pass filter.

By applying a smoothing filter, processing circuitry, e.g., processing circuitry 50, may attribute less weight to normal variations in daily temperature values when determining infection indication values, and instead determine infection indication values from less noisy signals. This is because high-frequency variations tend to be consistent day-to-day, but the actual amplitude of low frequency temperature values may still vary over time, for example, in response to the presence of infectious agents in the body. As such, a low pass filter may filter out high-frequency variations from the overall temperature values while allowing low frequency variations to still appear in the smoothened signal, as shown by the difference between FIGS. 7 and 8.

In some examples, processing circuitry, e.g., processing circuitry 50 of IMD 10, processing circuitry 80 of external device 12, or processing circuitry 98 of server 94, may determine a moving average of the plurality of temperature values over time to determine the smoothened signal. For example, processing circuitry 50 may compute a moving average of temperature values 702 to create smoothened signal 802. In some examples, processing circuitry 50 may employ a moving average filter to create a smoothened temperature signal, such as smoothened signal 802. The moving average may be based on a resolution parameter, such that the moving average is determined based on a resolution of daily, bidaily, hourly, etc. That is, processing circuitry 50 may compute the moving average on an hourly basis, daily basis, etc.

In some examples, processing circuitry 50 may determine the moving average of temperature values on a daily basis based on an average of temperature values from the week, month, or other arbitrary period of time prior to a current moving average determination. In a non-limiting example, processing circuitry 50 may determine the moving average of temperature values on day 10 by determining the average of the temperature values from the previous 10 days (days 1-10). In addition, processing circuitry 50 may determine the moving average of temperature values on day 11 by determining the average over the same period of time (days 2-11). In this way, processing circuitry 50 may determine the moving average based on a first-in, first-out (FIFO) buffer that stores finite amounts of temperature data over time (e.g., an X-day FIFO buffer). For example, the FIFO buffer may be a 10-day FIFO buffer that stores temperature values, average temperature values, moving averages of temperature values, etc. for 10 days at a time. In some examples, the moving average may be based on a plurality of moving averages determined over time. For example, a moving average on day 11 may be the sum of A2+A3+ . . . +A11 divided by 11, where A represents the average for the time period denoted by the subscript. For example, A1 may be the average temperature for day 1. A2 may be the average temperature value over days 1 and 2 or in some instances, A2 may be determined based on A1 and the average temperature from day 2. In another example, processing circuitry 50 may determine the moving average using exponential moving averages (EMA) or an otherwise weighted moving average (WMA).

In another example where the resolution comprises determining the moving average on a daily basis, processing circuitry 50 may determine the moving average on day 30 as the average of temperature values measured for the past 30 days and may determine the moving average on day 31 as the average or moving average of temperature values measured for the past 31 days. In any event, moving average filters may be used to create a constantly updated average temperature. In this way, a moving average filter may define a current directional trend for a set of temperature values.

In some examples, processing circuitry, e.g., processing circuitry 50 of IMD 10, processing circuitry 80 of external device 12, or processing circuitry 98 of server 94, may determine the infection status of the patient based at least in part on the infection indication value satisfying the threshold (612). For example, processing circuitry 50 may determine that the infection indication value exceeds the threshold or is otherwise equal to the threshold, and thus, satisfies the threshold. In some examples, the threshold may be set to a value based on empirical data. In an illustrative example, processing circuitry 50 may determine an infection indication value of 8.1 using the multiple low-pass-filter integration model. The infection indication value, in some examples, represents the integrated sum of the differences in temperature values. Accordingly, the infection indication value (e.g., 8.1 above) may be represented in units of temperature units nominally, such as degrees. In another example, the infection indication value may have units that depend on output of one of sensor(s) 62 (e.g., mV, mA, etc.). For example, one of sensor(s) 62 may be a temperature sensor that outputs values in millivolts (mV). Processing circuitry 50 may determine an integrated sum of differences as the infection indication value that are then represented in terms of the mV output of the respective sensor(s) 62. In some examples, the infection indication value and thresholds may be unitless values that increase, decrease or are set as described in the disclosure, and the particular values identified herein are merely examples that may vary based on the configuration of infection indication techniques for a particular patient, class of patients, particular temperature sensor or IMD, or class of temperature sensors or IMDs. The threshold for such a model may be set to be satisfied by difference values that are equal to or exceed 8.0 based on empirical data studies. Similarly, a threshold may be set for all or some of the infection detection models to encompass a range of threshold values, such that the threshold comprises a range of threshold values. A user or program may set the threshold or thresholds based on the type of detection model. In some instances, the thresholds may be based on empirical studies. The thresholds may be different for different detection models. For example, the multiple low-pass-filter detection model may have a threshold that differs from a threshold defined for the maximum-minimum detection model. In a non-limiting example and for illustration purposes only, the threshold for the multiple low-pass-filter detection model may be greater than 100 (e.g., 200), whereas the threshold for another detection model may be between 2 and 3 (e.g., 2.5). The difference in threshold values may differ because the type of detection model used may produce different ranges of output values.

In some examples, processing circuitry 50 may not apply the infection detection model until a predetermined amount of time has passed following implantation of IMD 10 or may not apply certain infection detection models during such initial time periods following implantation (e.g., recovery periods). For example, processing circuitry 50 may not apply the multiple low-pass-filter detection model during the initial recovery period and instead may apply a different detection model during that time period. In another example, processing circuitry 50 may apply one or more of the infection detection models to determine early device pocket infections, such as during a recovery period following implantation of IMD 10.

In some examples, processing circuitry 50 may not apply one or more of the filters described herein to determine various smoothened temperature signals until a predefined amount of time has elapsed from implantation. In a non-limiting and illustrative example, processing circuitry 50 may wait until 14-30 days have passed following device implantation. In any event, the predefined amount of time may be selected to coincide with a detected immune response (e.g., temperature spike following implantation) because the immune response may cause abnormal pocket temperatures until healing occurs or is complete. At the point of initialization, the filtered or smoothened temperature signals may be initialized. For example, the smoothened signals may be initialized to average the most recent X number of days' worth of temperature values. In one example, upon the predefined amount of time elapsing since implantation or following the immune response temperature increase, the smoothened signals may be determined based on an average of the most recent 4-days of temperature values.

In some examples, processing circuitry 50 may utilize an immune response of patient 4 when applying an infection detection model. For example, processing circuitry 50 may determine an immune response of patient 4 during the initial recovery period of patient 4 following implantation of IMD 10. As such, processing circuitry 50 may adjust parameters of the one or more of the infection detection models based on the particular immune system of patient 4. In some examples, processing circuitry 50 may determine that an initial reaction to implantation of IMD 10 has occurred based on an initial temperature change following implantation. Initial temperature changes may occur because of an immune response of patient 4 in the days following implantation of IMD 10. Processing circuitry 50 may determine an immune response metric for patient 4 based on the amplitude of the initial temperature increase. Processing circuitry 50 may utilize the immune response metric to adjust a parameter of any one of the detection models to improve the accuracy of the detection model. For example, processing circuitry 50 may automatically adjust a threshold parameter of a detection model based on the immune response metric specific to patient 4.

In some examples, processing circuitry, e.g., processing circuitry 50 of IMD 10, processing circuitry 80 of external device 12, or processing circuitry 98 of server 94, may determine infection indication values based on the infection detection model used (608). For example, processing circuitry 50 of IMD 10 may determine an infection indication value through application of the one or more sliding window detection models. In another example, processing circuitry 50 of IMD 10 may determine an infection indication value through application of the multiple low-pass-filter detection model.

In some examples, processing circuitry, e.g., processing circuitry 50 of IMD 10, processing circuitry 80 of external device 12, or processing circuitry 98 of server 94, may compare the infection indication value to a predefined threshold (610). For example, processing circuitry 50 of IMD 10 may employ a comparator to compare the infection indication value to the threshold. In some examples, the threshold may vary depending on which detection model is used. In some examples, the threshold may be a static threshold. In some examples, the threshold may comprise multiple staggered thresholds to serve as hysteresis thresholds.

In some examples, processing circuitry, e.g., processing circuitry 50 of IMD 10, processing circuitry 80 of external device 12, or processing circuitry 98 of server 94, may determine the infection status of the patient based at least in part on the infection indication value satisfying the threshold (612). For example, processing circuitry 50 may determine that the infection indication value exceeds the threshold or is otherwise equal to the threshold, and thus, satisfies the threshold. In some examples, the threshold may be set to a value based on empirical data. In an illustrative example, processing circuitry 50 may determine an infection indication value of 8.1 using the multiple pass filter integration model. The infection indication value, in some examples, represents the integrated sum of the differences in temperature values. Accordingly, the infection indication value (e.g., 8.1 above) may be represented in units of temperature units nominally, such as degrees. In another example, the infection indication value may have units that depend on output of one of sensor(s) 62 (e.g., mV, mA, etc.). For example, one of sensor(s) 62 may be a temperature sensor that outputs values in millivolts (mV). Processing circuitry 50 may determine an integrated sum of differences as the infection indication value that are then represented in terms of the mV output of the respective sensor(s) 62. In some examples, the infection indication value and thresholds may be unitless values that increase, decrease or are set as described in the disclosure, and the particular values identified herein are merely examples that may vary based on the configuration of infection indication techniques for a particular patient, class of patients, particular temperature sensor or IMD, or class of temperature sensors or IMDs. The threshold for such a model may be set to be satisfied by difference values that are equal to or exceed 8.0 based on empirical data studies. Similarly, a threshold may be set for all or some of the infection detection models to encompass a range of threshold values, such that the threshold comprises a range of threshold values. A user or program may set the threshold or thresholds based on the type of detection model. In some instances, the thresholds may be based on empirical studies. The thresholds may be different for different detection models. For example, the multiple low-pass-filter detection model may have a threshold that differs from a threshold defined for the maximum-minimum detection model. In a non-limiting example and for illustration purposes only, the threshold for the multiple low-pass-filter detection model may be greater than 100 (e.g., 200), whereas the threshold for another detection model may be between 2 and 3 (e.g., 2.5). The difference in threshold values may differ because the type of detection model used may produce different ranges of output values.

Depending on the general placement of the one or more temperature sensing devices, the infection status may indicate an infection in a device pocket of IMD 10. For example, the at least one temperature sensing device that determines temperature values over time, such as temperature values 702, may be located within or proximate a medical device, such as IMD 10 implanted in a device pocket of patient 4. As such, the infection status would likely indicate an infection in the device pocket of IMD 10. In some examples, an infection elsewhere in the body of patient 4 may also be detected by IMD 10 based on the infection indication value. In some examples, the temperature of IMD 10 may increase when the core body temperature of patient 4 increases, in which case, an increase in temperature may not be caused by a device pocket infection. However, in cases of device pocket infections, an increase in core body temperature of patient 4 may lag the temperature increase of IMD 10. In such instances, processing circuitry, e.g., processing circuitry 50 of IMD 10, processing circuitry 80 of external device 12, or processing circuitry 98 of server 94, may determine the infection indication value comprises an indication of a device pocket infection with respect to the implant site of IMD 10.

In some examples, processing circuitry 50 may receive temperature values for the core body temperature from another temperature sensing device, such as an external thermometer, and may compare the smoothened or raw temperature data to the core body temperature data to determine whether one temperature increase lags or leads another. In some instances, an increase in core body temperature due to a non-device pocket infection may cause an increase in IMD 10 temperature. In other instances, processing circuitry 50 may increase a confidence interval of a device pocket infection based on such comparisons. For example, when IMD 10 temperature increases so as to cause an infection indication value that exceeds a threshold, but where the core body temperature of patient 4 is not increasing at a particular rate, processing circuitry 50 may increase the confidence interval. As such, the confidence interval may indicate a high confidence that the increase in temperature of IMD 10 is likely an early indication of a device pocket infection.

In some examples, the system for determining infection status of a patient may include a plurality of temperature sensing devices that provide temperature values, where at least one temperature sensor is located within or fixed to IMD 10. The other one or more temperature sensing devices may be located within or fixed to IMD 10, whereas in some instances, some of the temperature sensing devices may also be located in or on other parts of the body of patient 4, such as with another IMD or external device in communication via network 92. A temperature sensing device may be of a different type or of the same type as the temperature sensing device of IMD 10 (e.g., sensor(s) 62). In some examples, the other temperature sensing device may be configured to measure core body temperature. In such examples, processing circuitry 50 may determine the plurality of temperature values over time based at least in part on temperature measurements from each of the temperature sensors. For example, processing circuitry 50 may determine the plurality of temperature values over time based at least in part on temperature measurements from each of the temperature sensors included with IMD 10.

In some instances, processing circuitry 50 may determine a high confidence interval for a device pocket infection of IMD 10, where one of sensor(s) 62 measures temperatures that cause an infection indication value that satisfies the threshold, but a second sensor of another IMD 10 or external medical device measures temperature values within a normal range or a range that does not indicate a separate bodily bacterial infection (e.g., ear, lung, skin, throat, bladder, or kidney infection or an otherwise non-device pocket infection). In some examples, the infection indication value from a temperature sensor device obtained from IMD 10 may be used to indicate separate bodily infections (e.g., ear, lung, skin, throat, bladder, kidney, etc.) because, for example, an increase in core temperature may lead or otherwise, precede, the increase in temperature of IMD 10. In this way, multiple temperature sensors may be used to determine whether a device pocket infection has occurred or whether another type of infection has occurred. In some instances, the multiple temperature sensors may be included with a single one of IMD 10. Similarly, temperature values from each of the multiple temperature sensors may be compared to determine whether temperature increases are sourced from a device pocket infection or whether the source of the temperature increase is elsewhere, away from IMD 10. For example, temperature values from a temperature sensor on the outside of IMD 10 may increase before temperature values from within IMD 10 indicating the temperature may not be increasing due to a device pocket infection. In some examples, processing circuitry 50 may also determine core body temperature and IMD 10 temperature values via one or more temperature sensing devices of IMD 10.

Although described as being performed by processing circuitry 50, these techniques may be performed by any one or more of IMD 10, external device 12, or server 94, e.g., by the processing or sensing circuitry of any one or more of these devices. For example, IMD 10 may transmit raw temperature data to external device 12, where external device 12 may determine the first infection indication values. In some examples, external device 12 may comprise multiple computing devices (e.g., a remote cloud server) that collectively determines the infection status of patient 4. In addition, it is to be understood that the components of system 2 (e.g., processing circuitry 50, processing circuitry 80, etc.) may perform some or all of the techniques described with reference to FIGS. 6-16 in parallel or in conjunction with one another. It should be noted that the above techniques of FIG. 6 may also be performed on a periodic basis.

Figure 9:
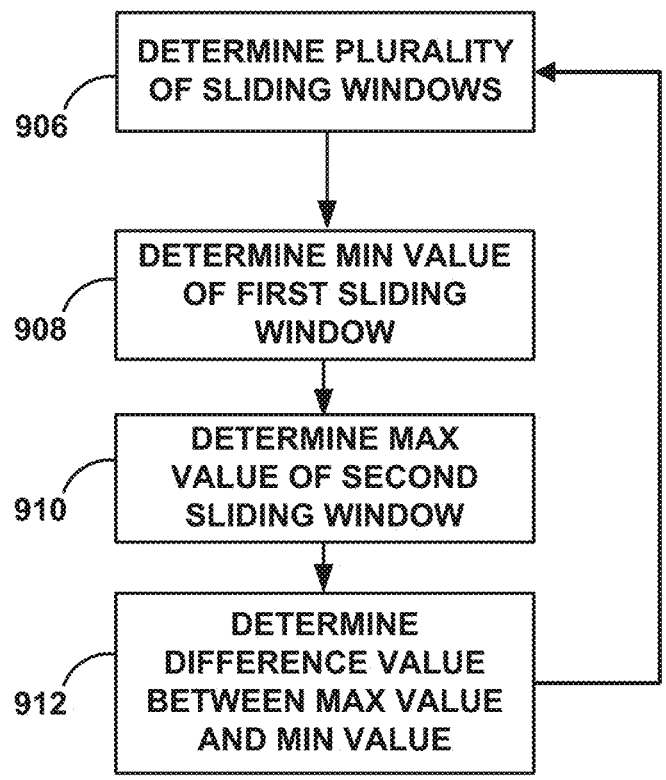
FIG. 9 is a flow diagram illustrating an example operation for sliding window detection for determining an infection status of a patient, in accordance with one or more techniques disclosed herein.

FIG. 9 is a flow diagram illustrating an example method for applying an example sliding window detection model to determine an infection status of patient 4, in accordance with one or more techniques of this disclosure. Although described as being performed by IMD 10, the example method of FIG. 9 may be performed by any one or more of IMD 10, external device 12, or server 94, e.g., by the processing circuitry or sensing circuitry of any one or more of these devices. For example, processing circuitry 50 may apply the detection model to determine the infection status of patient 4. Processing circuitry 50 may periodically apply the detection model to determine an infection status at various intervals. In some examples, processing circuitry 50 may determine an infection status in response to a user request for an infection status update. In some examples, external device 12 may determine the infection status of patient 4. For brevity, certain techniques are described with reference to IMD 10 (e.g., components of IMD 10 described with reference to FIG. 3). However, a person skilled in the art will understand that external device 12 and components of external device 12 may determine the infection status in some examples with input from IMD 10. In some examples, server 94 (e.g., a cloud server) may receive data from external device 12 or directly from IMD 10 and perform certain techniques of this disclosure.

In some examples, processing circuitry, e.g., processing circuitry 50 of IMD 10, processing circuitry 80 of external device 12, or processing circuitry 98 of server 94, may apply one or more of a maximum-minimum detection model or a rate of change detection model, as a sliding window detection model. For example, processing circuitry 50 may apply a maximum-minimum detection model as the sliding window detection model of FIG. 6. In another example, processing circuitry 50 may apply a rate of change detection model as the sliding window detection model of FIG. 6.

Figure 11:
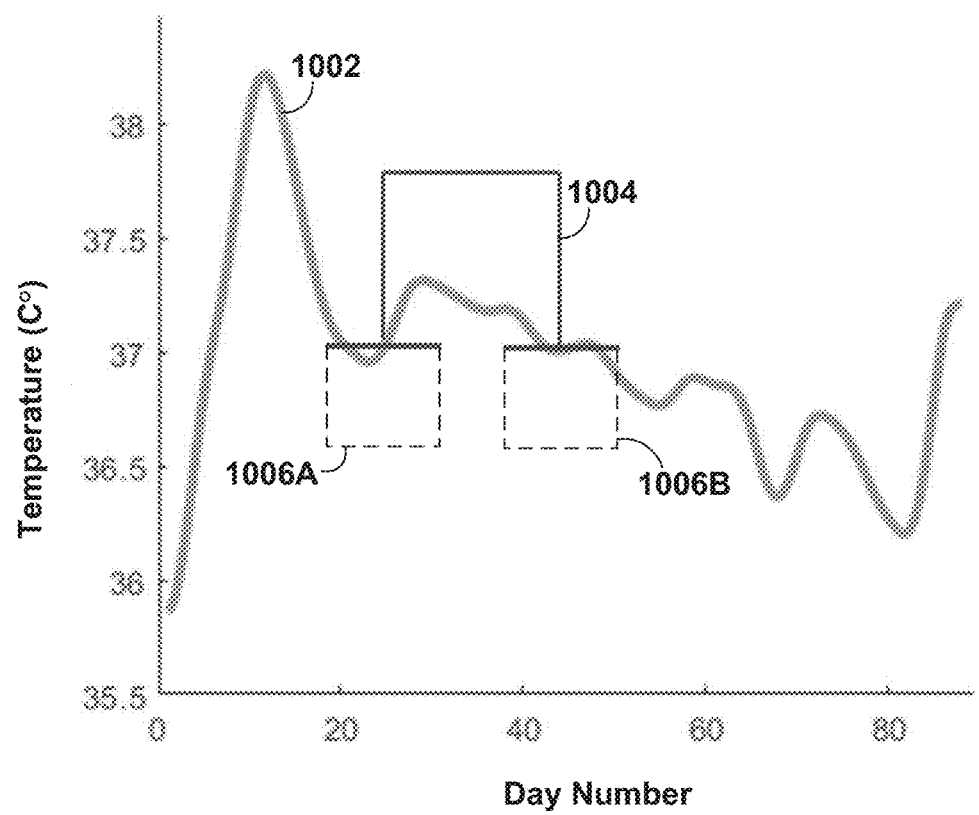
FIG. 11 is a conceptual graph illustrating an example operation for sliding window detection, in accordance with one or more techniques disclosed herein.

In the case of a maximum-minimum detection model, processing circuitry 50 may determine a plurality of sliding windows (906). For example, FIG. 11 illustrates an example smoothened temperature signal 1002, similar to smoothened temperature signal 802, having multiple sliding windows 1006A and 1006B. Sliding windows 1006A and 1006B comprise respective subsets of temperature data points of the smoothened temperature signal. In a non-limiting example, sliding window 1006A comprises temperature data points of the smoothened temperature signal from day 20 to day 30, whereas sliding window 1006B comprises temperature data points from day 40 to day 50.

In some examples, processing circuitry, e.g., processing circuitry 50 of IMD 10, processing circuitry 80 of external device 12, or processing circuitry 98 of server 94, may determine sliding windows to comprise a same number of days or other unit of time (e.g., hours). In some examples, the sliding windows may comprise a different number of days or other unit of time. For example, sliding window 1006A may cover a span of 10 days (or 10 hours), whereas sliding window 1006B may cover a span of 8 days. In another example, sliding window 1006A may cover a span of 10 hours, whereas sliding window 1006B may cover a span of 8 hours. The sliding parameters may be determined based on a center point for each window and adding and subtracting a particular number of days to obtain the window (e.g., 5 days, 6 days, etc.).

In an illustrative example, processing circuitry, e.g., processing circuitry 50 of IMD 10, processing circuitry 80 of external device 12, or processing circuitry 98 of server 94, may determine sliding window 1006A by starting from a first point and adding 5 days to the first point and subtracting 5 days to obtain sliding window 1006A. Similarly, second sliding window 1006B may be obtained using a second point offset by 5 days in both directions. As described below, the first and second points may coincide with the at least two temperature data points used for the rate of change detection model. That is, the first point may be a first temperature data point used for the rate of change detection model and the second point may be a second temperature data point, the first and second temperature data points defining sliding window 1004 used for the rate of change detection model. In some examples, the temperature data points for the rate of change detection model sliding window may be determined irrespective of windows 1006A and/or 1006B. In addition, first sliding window 1006A comprises temperature data points corresponding to an earlier period of time relative to second sliding window 1006B comprising temperature data points corresponding to a later period of time.

In some examples, processing circuitry, e.g., processing circuitry 50 of IMD 10, processing circuitry 80 of external device 12, or processing circuitry 98 of server 94, may determine a minimum temperature value of smoothened signal 1002 with respect to first sliding window 1006A (908). In addition, processing circuitry, e.g., processing circuitry 50 of IMD 10, processing circuitry 80 of external device 12, or processing circuitry 98 of server 94, may determine a maximum temperature value of smoothened signal 1002 with respect to second sliding window 1006B (910).

In some examples, processing circuitry, e.g., processing circuitry 50 of IMD 10, processing circuitry 80 of external device 12, or processing circuitry 98 of server 94, may determine a difference value between the maximum temperature value and the minimum temperature value (912).

For example, processing circuitry 50 may subtract the minimum temperature value from the maximum temperature value to determine the difference value. In some examples, processing circuitry 50 may determine difference values as a continuous loop, as indicated in FIG. 9. For example, processing circuitry may slide the plurality of sliding windows, such as by returning to determining a plurality of sliding windows, as indicated in FIG. 9.

In addition, processing circuitry, e.g., processing circuitry 50 of IMD 10, processing circuitry 80 of external device 12, or processing circuitry 98 of server 94, may compare the difference value to a predefined threshold (e.g., the threshold described with reference to FIG. 6). When the difference value satisfies the predefined threshold, processing circuitry, e.g., processing circuitry 50 of IMD 10, processing circuitry 80 of external device 12, or processing circuitry 98 of server 94, may determine an infection status. For example, processing circuitry 50 may determine the occurrence of a device pocket infection with respect to IMD 10 when the difference value for the maximum-minimum detection model exceeds a predefined threshold. If processing circuitry 50 determines the difference value does not satisfy the predefined threshold, the sliding window may shift and processing circuitry 50 may return to determining an updated plurality of sliding windows, as in performing a shift of the previous sliding windows (e.g., shift one hour, shift one day). For example, processing circuitry 50 may shift the sliding windows depending on a resolution parameter defining how often processing circuitry 50 is to determine the presence of an infection using one or more of the infection detection models.

Figure 10:
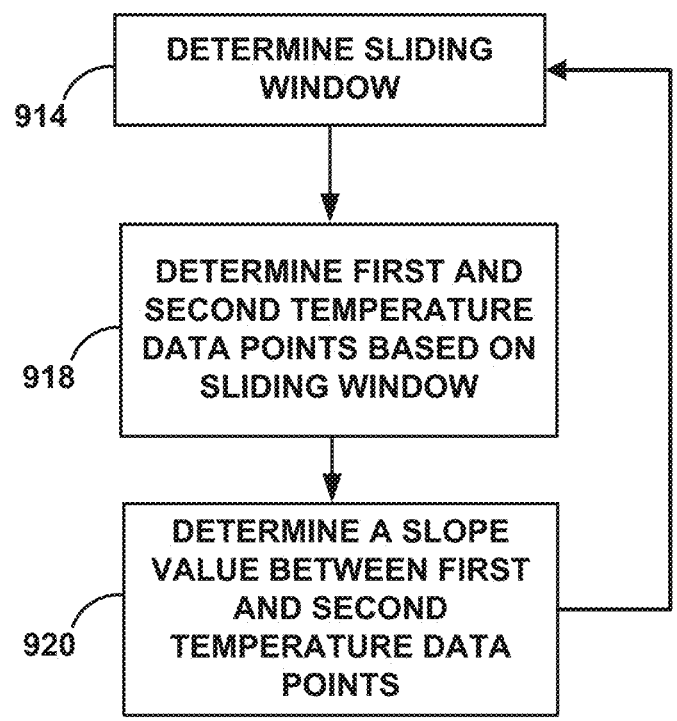
FIG. 10 is a flow diagram illustrating another example operation for sliding window detection for determining an infection status of a patient, in accordance with one or more techniques disclosed herein.

FIG. 10 is a flow diagram illustrating an example method for applying an example rate of change detection model to determine an infection status of patient 4, in accordance with one or more techniques of this disclosure. Although described as being performed by IMD 10, the example method of FIG. 10 may be performed by any one or more of IMD 10, external device 12, or server 94, e.g., by the processing circuitry or sensing circuitry of any one or more of these devices. For example, processing circuitry 50 may apply the rate of change detection model to determine the infection status of patient 4. Processing circuitry 50 may periodically apply the rate of change detection model to determine an infection status at various intervals. In some examples, processing circuitry 50 may determine an infection status in response to a user request for an infection status update. In some examples, external device 12 may determine the infection status of patient 4. For brevity, certain techniques are described with reference to IMD 10 (e.g., components of IMD 10 described with reference to FIG. 3). However, a person skilled in the art will understand that external device 12 (e.g., components of external device 12) may determine the infection status in some examples with input from IMD 10. In some examples, server 94 (e.g., a cloud server) may receive data from external device 12 or directly from IMD 10 and perform certain techniques of this disclosure.

In some examples, processing circuitry, e.g., processing circuitry 50 of IMD 10, processing circuitry 80 of external device 12, or processing circuitry 98 of server 94, may apply the rate of change detection model as the sliding window detection model of FIG. 6. For example, processing circuitry 50 may determine a sliding window (914). In an illustrative example, the sliding window may include temperature data points of smoothened temperature signal 1002. For example, the sliding window may include sliding window 1004 illustrated as a sliding box for illustration purposes. Sliding window 1004 may be used to look at data retroactively. In some examples, sliding windows 1004 (and sliding window 1006B described with reference to FIG. 9) may be applied to current temperature data as the temperature data is collected in real-time. In such examples, the right edge of sliding window 1004 or the right edge of sliding window 1006B may correspond to the current most temperature data collected from IMD 10. In some examples, sliding window 1004 may be a fixed time window that slides both edges of sliding window 1004 at a same rate. In some examples, the parameters of sliding window 1004 may be set by a user. For example, processing circuitry 50 may receive user input specifying the parameters of sliding window 1004, or sliding windows 1006, defining whether or not the sliding window is fixed and if so, how the outer edges of the sliding window will be defined or spaced apart over time.

In some examples, processing circuitry, e.g., processing circuitry 50 of IMD 10, processing circuitry 80 of external device 12, or processing circuitry 98 of server 94, may determine temperature data points based on the sliding window (918). For example, processing circuitry 50 may determine at least two temperature data points of sliding window 1004. In such examples, processing circuitry 50 may determine a first temperature data point and a second temperature data point of sliding window 1004. For example, processing circuitry 50 may determine a first temperature data point as corresponding to the left-most data point of sliding window 1004 and a second temperature data point as corresponding to the right-most data point of sliding window 1004, where the right-most temperature data point may correspond to a temperature value most-recently determined by IMD 10.

In some examples, processing circuitry, e.g., processing circuitry 50 of IMD 10, processing circuitry 80 of external device 12, or processing circuitry 98 of server 94, may determine a slope value between at least two temperature data points (920). In an illustrative example, FIG. 11 illustrates a sliding window 1004 defined by at least two temperature data points. In such an example, processing circuitry 50 may determine a slope value between the first and second temperature data points of sliding window 1004 (e.g., where sliding window 1004 intersects signal 1002). Although the temperature data points in FIG. 11 are illustrated as being spaced approximately 20 days apart, the techniques of this disclosure are not so limited, and processing circuitry 50 may determine the sliding window to have temperature data points spaced farther apart or closer together in various examples. In a non-limiting example, processing circuitry 50 may determine the at least two temperature data points for the sliding window to be spaced 1-3 days apart. Sliding windows 1006A and 1006B may, in some examples, follow a similar pattern so as to have a center point spaced 1-3 days apart. In other examples, the sliding windows may include more or less of a time span. For example, sliding window 1004 or sliding windows 1006 may include more than 3 days' worth of temperature data or less than 1 days' worth of data. In one example, sliding window 1006A may include 6 hours' worth of temperature data collected immediately prior to day 21 and 6 hours' worth of temperature data collected consecutively thereafter for a total of 12 hours' worth of temperature data defining sliding window 1006A In some examples, processing circuitry, e.g., processing circuitry 50 of IMD 10, processing circuitry 80 of external device 12, or processing circuitry 98 of server 94, may compare the slope values to a predefined threshold (e.g., the threshold described with reference to FIG. 6). When the slope value satisfies the predefined threshold, processing circuitry, e.g., processing circuitry 50 of IMD 10, processing circuitry 80 of external device 12, or processing circuitry 98 of server 94, may determine an infection status. For example, processing circuitry 50 may determine the occurrence of a device pocket infection with respect to IMD 10 when the slope value for the rate of change detection model exceeds a predefined threshold. If not, processing circuitry 50 may return to determining an updated sliding window and determining a slope value between updated temperature data points that define the updated sliding window. For example, processing circuitry 50 may shift sliding window 1004 forward in time by a predefined interval. In some examples, the sliding windows may be applied retroactively to data points collected over time. In some examples, the sliding windows may be applied to current temperature data as the temperature data is collected, such that the sliding window may slide at a same rate as the sampling rate for the temperature data or otherwise synchronized with the creation of smoothened temperature signals.

As noted before with respect to FIG. 6, the above techniques of FIG. 10 may also be performed on a periodic basis. For example, the temperature values may be determined according to a resolution parameter setting of IMD 10 (e.g., the resolution parameter used to signal a frequency at which sensor(s) 64 should probe for temperature measurements). In other examples, the infection indication values may be calculated irrespective of the resolution parameter. For instance, IMD 10 may identify the infection status at several time intervals each day (e.g., once in the morning, once in the afternoon, once in the evening, once after meals, etc.). IMD 10 may identify the infection status once a day, each week, every two weeks, each month, etc.

In some examples, IMD 10 may also identify the infection status in response to a user command (e.g., from a physician, from a user interface) or in response to a satisfaction of another condition (e.g., based on activity level or other physiological parameters). For example, IMD 10 may identify the infection status on a per measurement basis, such as on a per temperature value measurement basis. A person of skill in the art will appreciate that various periods may exist for when IMD 10 or external device 12 may transmit infection statuses, temperature values, and/or smoothened temperature values, and/or otherwise, identify infection statuses for subsequent analysis.

In addition, in some instances, multiple sliding window detection models may be used in tandem in order to determine the infection status of patient 4. For example, in some instances, the rate of change detection model may be used in conjunction with the maximum-minimum detection model. In one example, processing circuitry 50 may combine the difference value determined using the maximum-minimum detection model with the slope value determined using the rate of change detection model. For example, processing circuitry 50 may add the values determined from the respective detection models together. In addition, processing circuitry 50 may multiply each value from the respective detection models by a predefined weighting parameter in order to scale the respective values. In some examples, processing circuitry 50 may perform the scaling prior to combining the values. In any case, processing circuitry 50 may determine the infection status of patient 4 by determining whether the combined value exceeds a predefined threshold. The predefined threshold may be the same or different from the predefined threshold used for any of the detection models individually (e.g., multiple low-pass-filter integration model, rate of change detection model, etc.).

Figure 12:
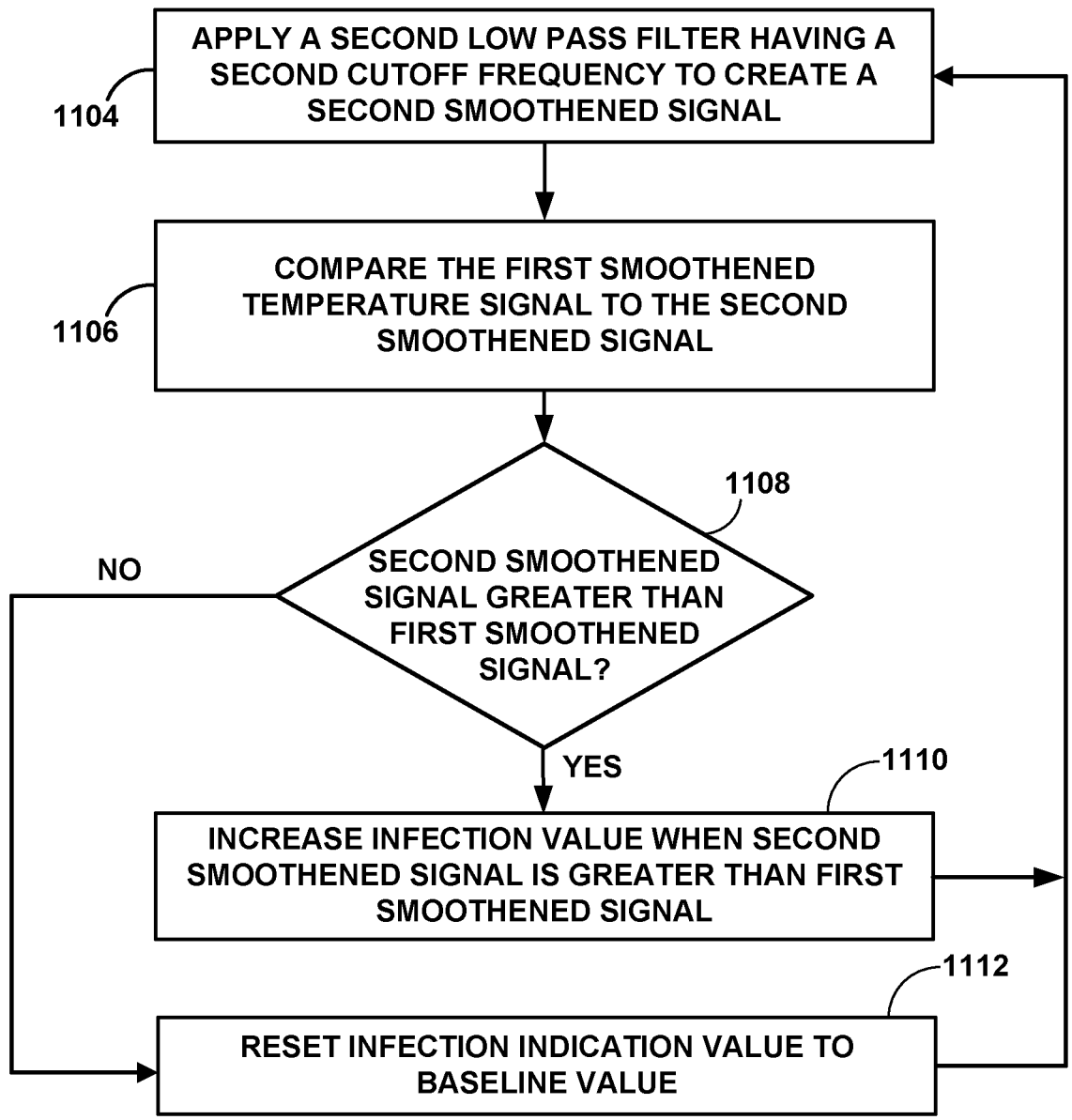
FIG. 12 is a flow diagram illustrating an example operation for multiple low-pass filter integration detection for determining an infection status of a patient, in accordance with one or more techniques disclosed herein.

FIG. 12 is a flow diagram illustrating an example method for applying detection models to determine an infection status of patient 4, in accordance with one or more techniques of this disclosure. Although described as being performed by IMD 10, the example method of FIG. 12 may be performed by any one or more of IMD 10, external device 12, or server 94, e.g., by the processing circuitry or sensing circuitry of any one or more of these devices. For example, processing circuitry 50 may apply the detection model to determine the infection status of patient 4. Processing circuitry 50 may periodically apply the detection model to determine an infection status at various intervals. In some examples, processing circuitry 50 may determine an infection status in response to a user request for an infection status update. In some examples, external device 12 may determine the infection status of patient 4. For brevity, certain techniques are described with reference to IMD 10 (e.g., components of IMD 10 described with reference to FIG. 3). However, a person skilled in the art will understand that external device 12 and components of external device 12 may determine the infection status in some examples with input from IMD 10. In some examples, server 94 (e.g., a cloud server) may receive data from external device 12 or directly from IMD 10 and perform certain techniques of this disclosure.

In some examples, processing circuitry, e.g., processing circuitry 50 of IMD 10, processing circuitry 80 of external device 12, or processing circuitry 98 of server 94, may apply a multiple low-pass-filter integration model. As such, FIG. 12 is an example of a multiple low-pass-filter integration model being used as the infection detection model.

In some examples, processing circuitry 50 may apply a second low pass filter having a second cutoff frequency to the temperature values determined over time to create a second smoothened signal (1104). In such examples, the first smoothened signal may comprise the signal obtained through application of a first low pass filter to the plurality of temperature values. The first low pass filter may be the same as the first low pass filter above described with reference to the other infection detection models. In other examples, the first low pass filter used to create the first smoothened signal in the multiple low-pass-filter integration model may not be the same low pass filter. For example, the low pass filters may have different cutoff frequencies. In any case, the first low pass filter may have a first cutoff frequency that differs from the second cutoff frequency. For example, the first low pass filter may have a first cutoff frequency that is less than the second cutoff frequency. In such examples, processing circuitry 50 may then have applied two filters to create two different smoothened signals. The two smoothened signals may then be compared to one another as described below.

In one illustrative example, the low pass filter used to obtain the first smoothened temperature signal and the second smoothened temperature signal may include a type of low pass filter that is a moving average filter. For example, processing circuitry 50 may use a moving average filter having a first setting (e.g., window size) to obtain the first smoothened signal. The first setting may include a window size of X number of samples. In a non-limiting and illustrative example, processing circuitry 50 may set the window size at a nominal 10 samples for the sliding window. In such examples, 10 samples may correspond to 2.5 days when processing circuitry 50 employs a sampling rate of 4 samples/day. Similarly, processing circuitry 50 may utilize the moving average filter having a second setting to obtain the second smoothened signal. The second setting may correspond to a setting that utilizes an increased amount of filtering compared to the first setting. For example, processing circuitry 50 may use a second setting that obtains a nominal moving average that is more filtered than the first setting. For example, processing circuitry 50 may set the second setting to include a window size of Y number of samples, where Y is greater than X. In a non-limiting example, Y may be 20 samples, which in the above example, may correspond to 5 days at 4 samples/day. In any case, processing circuitry 50 may utilize one or more filters having various filter settings (e.g., window sizes, cutoff frequencies, etc.) to obtain the first smoothened signal and the second smoothened signal.

Figure 13:
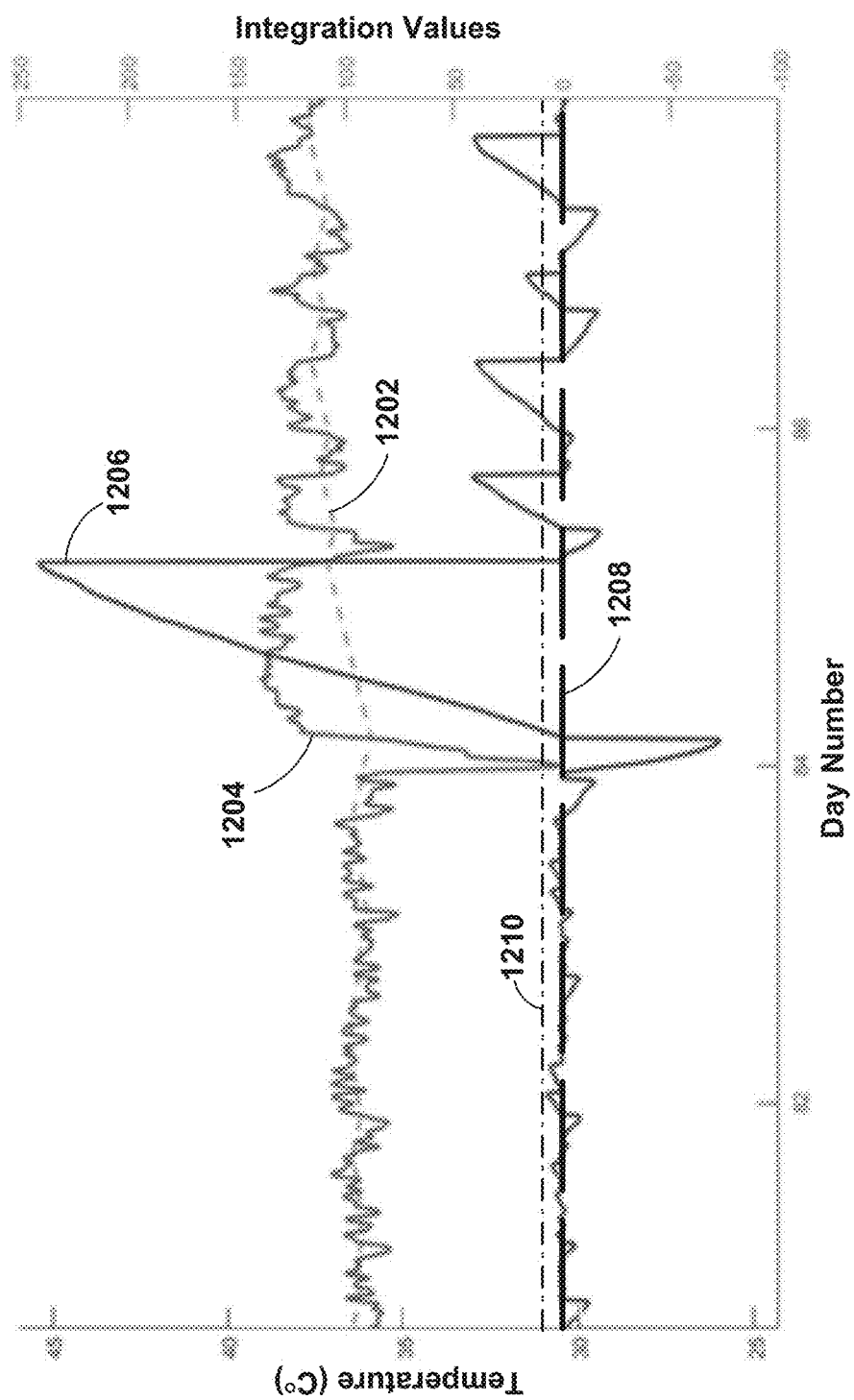
FIG. 13 is a conceptual graph illustrating an example operation for a multiple low-pass filter integration model, in accordance with one or more techniques disclosed herein.

In some examples, processing circuitry, e.g., processing circuitry 50 of IMD 10, processing circuitry 80 of external device 12, or processing circuitry 98 of server 94, may compare the first smoothened temperature signal to the second smoothened signal (1106). FIG. 13 illustrates an example graph of a first smoothened signal 1202 and a second smoothened signal 1204. As such, processing circuitry may determine whether or not second smoothened signal 1204 is greater than first smoothened signal 1202 (1108).

In some examples, processing circuitry, e.g., processing circuitry 50 of IMD 10, processing circuitry 80 of external device 12, or processing circuitry 98 of server 94, may increase the infection indication value when second smoothened signal 1204 is greater than first smoothened signal 1202 (1110). FIG. 13 illustrates an example infection indication value 1206 increasing when second smoothened 1204 is greater than first smoothened signal 1204. In some examples, the amount of the increase to infection indication value 1206 may be equal to or proportional to the difference between values corresponding to first smoothened signal 1202 and second smoothened signal 1204. In this way, the integrated difference between values corresponding to first smoothened signal 1202 and second smoothened signal 1204 is represented as infection indication value 1206.

In some instances, the infection indication value 1206 may increase or decrease proportional to the difference between values corresponding to first smoothened signal 1202 and second smoothened signal 1204, rather than necessarily being equal to the difference between values corresponding to first smoothened signal 1202 and second smoothened signal 1204. For example, the infection indication value 1206 may increase at X times the difference value and may decrease at Y times the difference value, where X and Y may or may not have the same proportional multiplier or fractional value. For example, X may equal 0.5, 1, or 2, etc., while Y may equal the same or a different value. In this way, the integration difference between values corresponding to first smoothened signal 1202 and second smoothened signal 1204 may be scaled in order to determine the increase and decrease intervals for infection indication value 1206. The proportional difference values (e.g., X or Y) may be predefined by a user (e.g., clinician) and implemented by processing circuitry, e.g., processing circuitry 50 of IMD 10, processing circuitry 80 of external device 12, or processing circuitry 98 of server 94, when determining how much to increase or decrease infection indication value 1206.

In some examples, the calculation of difference values between corresponding values of first smoothened signal 1202 and second smoothened signal 1204 may be constrained to occur over a predefined window of recent time. The predefined window of time may be an integer number of 24-hour days. Processing circuitry 50 may use 24-hour days as the predefined window because circadian variation in temperature tend to naturally create a difference between first smoothened signal 1202 and second smoothened signal 1204 within a 24-hour period. That is, past temperature measurements may become obsolete and thus, the integration calculation for difference values may allow the past temperature measurements to be subtracted from the final integral difference value, unless the infection indication value has been reset in the meantime.

In addition, processing circuitry, e.g., processing circuitry 50 of IMD 10, processing circuitry 80 of external device 12, or processing circuitry 98 of server 94, may reset infection indication value 1206 to a baseline value when second smoothened 1204 is not greater than first smoothened signal 1202. For example, processing circuitry 50 may reset infection indication value 1206 to a baseline value when second smoothened signal 1204 equals first smoothened signal 1202 or is less than first smoothened signal 1202 (1112). It should be noted that while shown as comprising a negative number below baseline value 1208 in FIG. 13, infection indication value 1206 in some instances, may be reset to baseline value 1208 (e.g., zero) and may not decrease any further than baseline value 1208. In other words, infection indication value 1206 may flat line at zero as long as the second smoothened signal 1204 is less than or equal to first smoothened signal 1202.

In an illustrative example, processing circuitry 50 may decrease infection indication value 1206 as low as baseline value 1208. For example, if baseline value 1208 is set to equal zero, processing circuitry 50 may continue to decrease infection indication value 1206 when proper conditions are met until infection indication value 1206 reaches baseline value 1208 of zero (e.g., a stop limit). Processing circuitry 50 may then increase infection indication value 1206 above baseline value 1208 when proper conditions are met for increasing infection indication value 1206. In other examples, processing circuitry 50 may decrease infection indication value 1206 when second smoothened signal 1202 is less than first smoothened signal 1202 without a stop limit. For example, as shown in FIG. 13, processing circuitry 50 may, in some instances, decrease infection indication value 1206 below baseline value 1208, rather than stopping the decrease at baseline value 1208 as discussed above. In an illustrative example, FIG. 13 illustrates the baseline value 1208 as being equal to zero.

Once the infection value has been increased (1110) or reset to baseline value 1208 (1112), processing circuitry 50 may return to applying the second low pass filter to one or more updated temperature values determined over time to create an updated second smoothened signal. In addition, processing circuitry 50 may apply the first low pass filter to the updated temperature values determined over time to create an updated first smoothened signal. Processing circuitry 50 may determine an updated infection value using the updated smoothened signals in accordance with various techniques of this disclosure. As shown in FIG. 13, infection indication values may be integration values determined as the integral or difference total between smoothened signals. As such, processing circuitry 50 may determine the integration values by determining the difference between temperature values of the smoothened signals using an integral determination.

In some examples, processing circuitry, e.g., processing circuitry 50 of IMD 10, processing circuitry 80 of external device 12, or processing circuitry 98 of server 94, may compare the increasing infection indication value to a predefined threshold and may determine, based at least in part on the infection indication value satisfying the predefined threshold, an infection status of patient 4. For example, FIG. 13 illustrates the predefined threshold 1210 as being equal to approximately 8.0. In such examples, where infection indication value 1206 exceeds the predefined threshold 1210, processing circuitry, e.g., processing circuitry 50 of IMD 10, processing circuitry 80 of external device 12, or processing circuitry 98 of server 94, may determine the occurrence of a device pocket infection.

Figure 14:
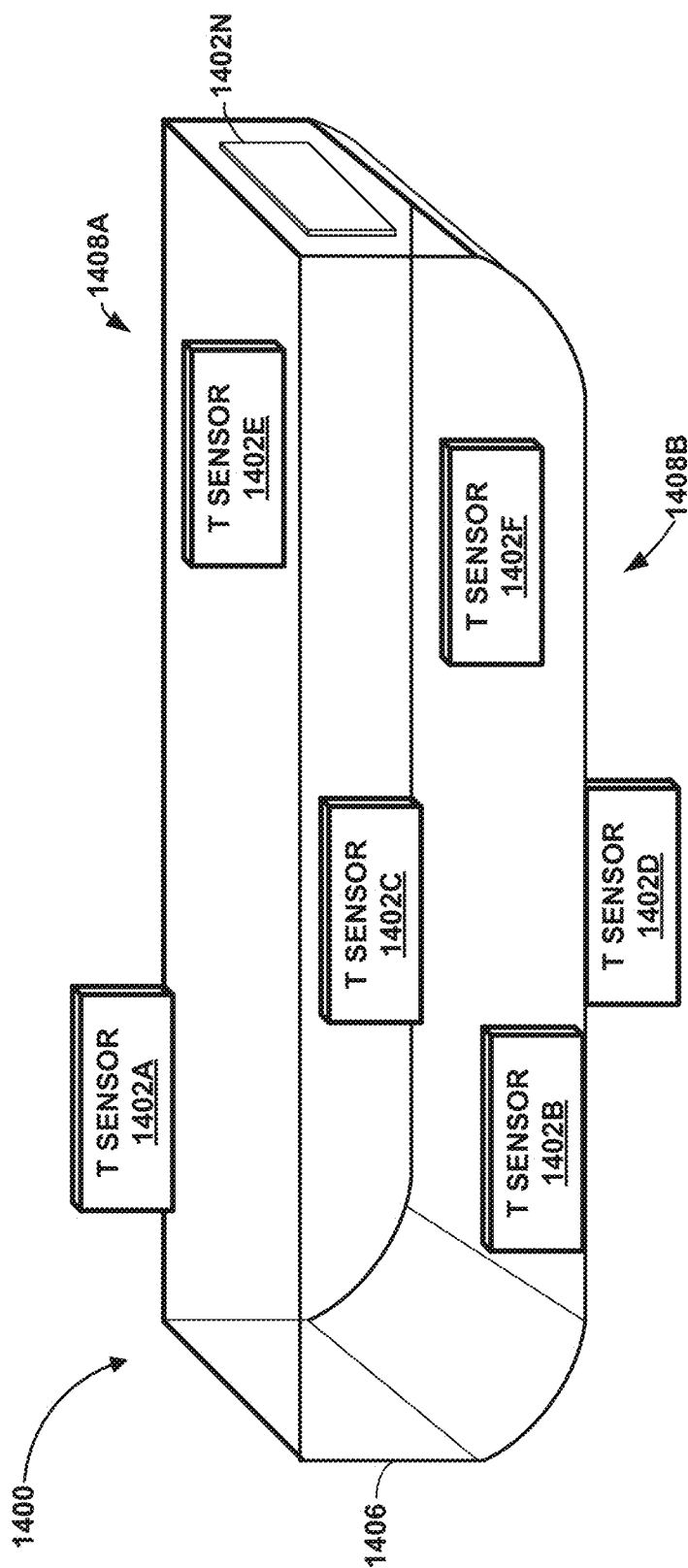
FIG. 14 is a block diagram illustrating an example system that includes multiple temperature sensing devices, in accordance with one or more techniques disclosed herein.

FIG. 14 is a block diagram illustrating an IMD 1400 having multiple sensors 1402A-N, such as sensor(s) 62 of IMD 10. IMD 1400 is an example configuration of IMD 10. Housing 1406 is an example of housing 15. Temperature sensors 1402A-N are examples of sensor(s) 62 placed inside and outside of IMD 1400. Although shown as blocks, the sensors may include wires, resistive devices, or other elements configured to measure temperature. For example, sensor 1402A may be a temperature sensor configured as a lead or other element extending outward from IMD 1400 to measure temperature around the perimeter of IMD 1400. At least two of sensors 1402 are temperature (T) sensors. In some instances, other non-temperature sensing devices may also be included, such as additional sensor(s) 62 in and around IMD 1400. In some instances, one of T sensors 1402 may be configured to perform additional sensing, such as motion sensing, etc. In any case, T sensors 1402 may be positioned on the insides, or on the outsides of IMD 1400, as shown. For example, T sensor 1402A may be placed around IMD 1400 so as to be fixed to a top, bottom, or side of IMD 1400. Processing circuitry, e.g., processing circuitry 50 of IMD 10, processing circuitry 80 of external device 12, or processing circuitry 98 of server 94, may use data from multiple T sensors 1402 to determine a rate a heat loss rate from patient 4 for certain environmental factors. For example, a heat loss rate may be based on ambient temperature conditions, clothing insulative characteristics, and also activity thermodynamics that cause heat loss from a patient at quantifiable rates.

In some examples, IMD 1400 may interface with or include multiple temperature sensing devices 1402A-N. In some examples, processing circuitry, e.g., processing circuitry 50 of IMD 10, processing circuitry 80 of external device 12, or processing circuitry 98 of server 94, may receive and compare temperature values from at least two of sensors 1402A-N to derive one or more temperature gradients between multiple locations within patient 4. For example, processing circuitry 50 may cross correlate temperature value data to infer device pocket temperature changes or core body temperature changes. Further processing circuitry may determine which temperature change precedes the other. For example, if an increase in core body temperature follows an increase in device pocket temperature increase, then processing circuitry 50 may infer that the source of the temperature increase is from within the device pocket. Therefore, such a temperature gradient likely indicates a device pocket infection that has now or has the potential to lead to an increase in core body temperature, as in a febrile event in patient 4.

In one illustrative example, using multiple temperature sensing devices may provide spatial resolution to the temperature gradient. For example, processing circuitry 50 may be able to determine improved diagnostics for febrile sensitivity relative to environment factors and infection temperature sensitivity. In some examples, IMD 10 may reside in a subcutaneous tissue pocket with leads that extend to a site of therapy. Device infections (e.g., pocket infections) typically occur first within the subcutaneous device pocket. In some instances, the infection can spread from IMD 10 to the site of therapy. Using multiple temperature sensing devices on leads extending away from housing 1406, from the site of therapy, or from other locations may allow processing circuitry 50 to detect such infections early. In one example, a temperature sensor may be added to a cardiac lead that provides temperature values to processing circuitry, such as processing circuitry 50 of IMD 10, processing circuitry 80 of external device 12, or processing circuitry 98 of server 94.

Any suitable sensor(s) 62 or temperature sensor devices may be used to detect temperature or changes in temperature. In some examples, sensor(s) 62 may include a thermocouple, a thermistor, a junction-based thermal sensor, a thermopile, a fiber optic detector, an acoustic temperature sensor, a quartz or other resonant temperature sensor, a thermo-mechanical temperature sensor, a thin film resistive element, etc. In some examples, calibration of temperature sensors will be performed at the time of manufacture with each sensor calibrated and/or trimmed for absolute temperature measurement.

Figure 15:
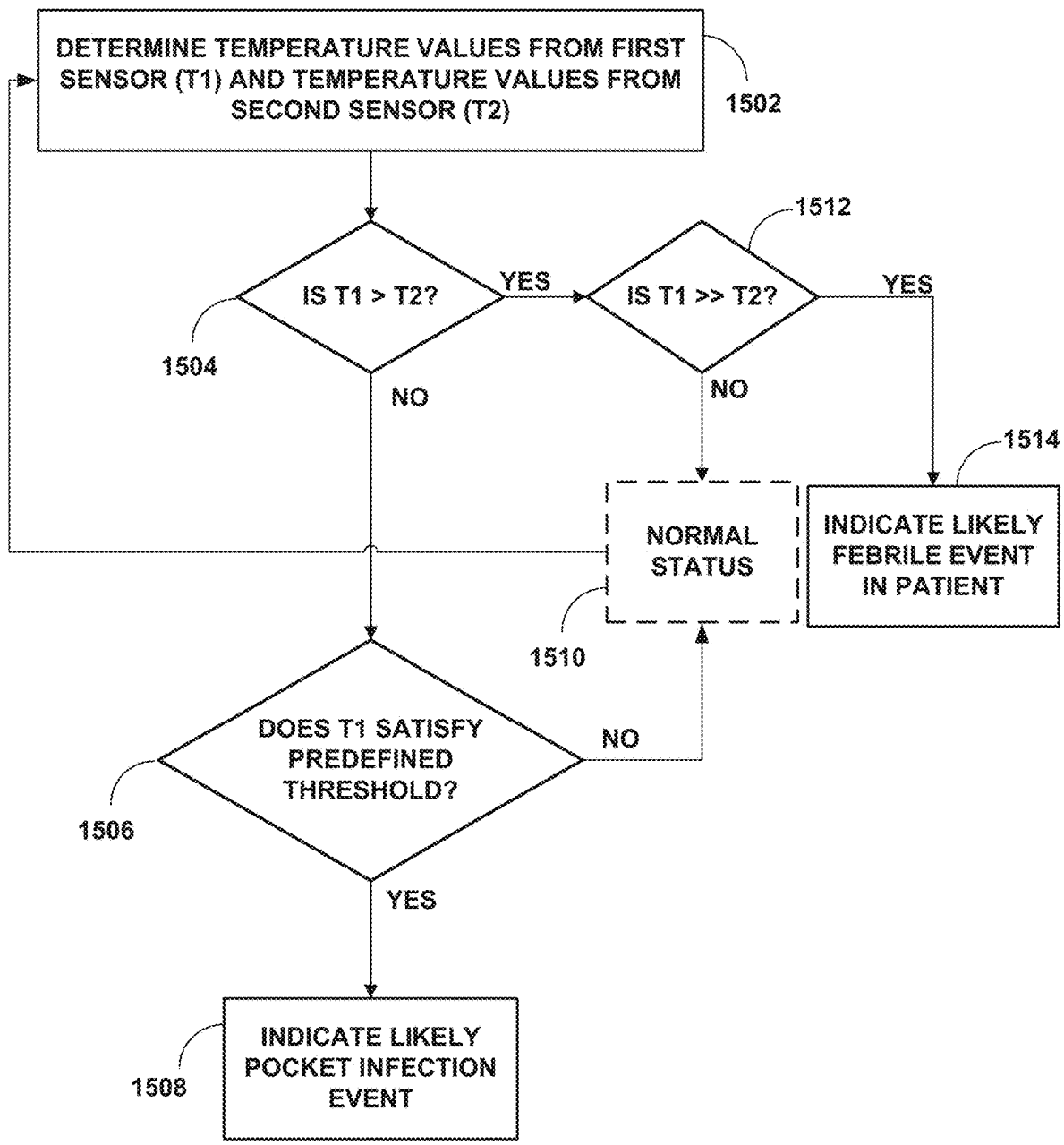
FIG. 15 is a flow diagram illustrating an example method that may be performed by one or both the IMD and external device shown in FIG. 1 to determine an infection status of the patient using separate temperature values, in accordance with one or more techniques disclosed herein.

FIG. 15 is a flow diagram illustrating an example method that may be performed by one or both the IMD 10 and/or one or more external devices, such as at least one of external device 12, to determine an infection status of patient 4 using separate temperature values (e.g., temperature values obtained from multiple temperature sensors, separate temperature values obtained from a temperature sensor measuring temperature at various locations in and/or around IMD 10, etc.), in accordance with one or more techniques of this disclosure.

Although described as being performed by IMD 10, the example method of FIG. 15 may be performed by any one or more of IMD 10, external device 12, or server 94, e.g., by the processing circuitry or sensing circuitry of any one or more of these devices. For example, processing circuitry 50 may receive multiple temperature values from multiple temperature sensors, such as multiple sensors 62 or 1402. In some examples, processing circuitry 50 may transmit via communication circuitry 54, the temperature values to another device, such as external device 12. In such examples, external device 12 may receive the temperature values from IMD 10 and determine the infection status of patient 4 based on the multiple temperature values. For brevity, certain techniques are described with reference to IMD 10 (e.g., components of IMD 10 described with reference to FIG. 3). However, a person skilled in the art will understand that server 94 (e.g., components of server 94) may determine the infection status in some examples with input from IMD 10 and/or external device 12. For example, server 94 may receive temperature data, IMD orientation data, etc. from external device 12 and/or IMD 10 and perform certain techniques of this disclosure.

In some examples, external device 12 may be a separate device, such as a wearable device, an external/portable device, etc. configured to measure core body temperature, or other temperature related measurements, of patient 4. For example, external device 12 may include a temperature sensing device. As such, processing circuitry 80 of external device 12 may transmit temperature values to another device, such as IMD 10 or server 94, via communication circuitry 82. In any case, processing circuitry, such as processing circuitry 50 of IMD 10, processing circuitry 80 of external device 12, or processing circuitry 98 of server 94, may use such temperature values, in addition to temperature values obtained from temperature sensors of IMD 10, in order to determine infection status of patient 4, such as by cross-correlating temperature data and identifying a source/origin of an infectious event (e.g., in the pocket of IMD 10).

In one example method, processing circuitry, such as processing circuitry 50 of IMD 10, processing circuitry 80 of external device 12, or processing circuitry 98 of server 94, may determine temperature values from at least two sensors (1502). For example, processing circuitry 50 may determine one or more temperature values (e.g., first temperature values) from a first sensor (e.g., T1 temperature values). Processing circuitry 50 may also determine one or more temperature values (e.g., first temperature values) from a second sensor (e.g., T2 temperature values). In some examples, the first sensor may include a body side sensor (e.g., Tb) and the second sensor may include a skin side sensor (Ts). In other examples, processing circuitry 50 may determine one or more temperature values from multiple temperature sensors positioned in and around IMD 10 or in some instances, received from another device, such as one of external devices 12.

In some examples, e.g., when configured as illustrated with respect to IMD 1400 of FIG. 14, IMD 10 may have one side comprising a relatively flat surface 1408A and another side of IMD 10 comprising a curved surface 1408B that is less flat than flat surface 1408A. In some examples, the curved surface 1408B may extend around the side walls of IMD 10 and to flat surface 1408A. For example and for visual illustration purposes with reference to the example IMD 1400 of FIG. 14, a side wall of IMD 10 may include a side having sensor 1402N, for example, such that in some examples, curved surface 1408B and flat surface 1408A are adjoined at the ends of each surface.

IMD 10 may be positioned with flat surface 1408A oriented so as to be against or adjacent a muscle of patient 4 and curved surface 1408B may face toward the skin of the chest (e.g., skin side of IMD 10). In such examples, a body side sensor may be positioned on flat side, such as on the inside of IMD 10 on the side of flat surface 1408A, and a skin side sensor may be positioned on the curved side of IMD 10. The orientation of IMD 10 may be controlled so as to be consistent across other patients. That is, the orientation may provide a normal, known, or otherwise trackable positioning of each sensor. In any case, the orientation may be selected to coincide with the primary direction of temperature gradient.

By implanting VIMD 10 to have a body side sensor positioned inside IMD 10 on the flat side of IMD 10 and a skin side sensor on the curved side of IMD 10, processing circuitry 50 may utilize temperature values received from at least the two separately located sensors in order to identify temperature gradients at IMD 10 and use the identified temperature gradient information to deduce whether an increase in infection indication value is caused by an infection at IMD 10 or another region of patient 4. In addition, processing circuitry 50 may use data from other sensors (e.g., temperature sensors) to provide additional resolution and/or confirmation of temperature values and infection origin locations.

In some examples, processing circuitry may determine the orientation of IMD 10, and certain sensors of IMD 10, from accelerometer data of IMD 10 or patient 4. In an example of accelerometer data of patient 4, patient 4 may have a wearable device that tracks the orientation of patient 4, such that processing circuitry may infer or deduce the orientation of IMD 10 and sensors therein or sensors extending therefrom, such as from one or more leads. Processing circuitry 50 may use such data to determine a direction of a temperature gradient increase and determine whether an increase in infection indication value is caused by an infection at IMD 10 or another region of patient 4.

In one example, processing circuitry, such as processing circuitry 50 of IMD 10, processing circuitry 80 of external device 12, or processing circuitry 98 of server 94, may determine whether T1 is greater than T2 (1504). For example, processing circuitry 50 may determine that one or more temperature values (e.g., an average temperature) from a body side sensor is less than or equal to one or more temperature values from a skin side sensor (NO branch to 1506). In such instances, processing circuitry 50 may determine whether T1 satisfies a predefined threshold (1506). If so (YES branch to 1508), processing circuitry 50 may indicate the likely event of an infection originating at IMD 10 (e.g., a device pocket infection). That is, processing circuitry 50 may attribute the increase in infection indication value to a likely device pocket infection. In some examples, IMD 10 may do so by increasing a confidence interval indicative of the likelihood an infection source is at IMD 10 or otherwise, attributed to another cause such as a separate febrile event in patient 4 (e.g., influenza). In any case, based on the event indication and/or high confidence interval, processing circuitry 50 may provide an alert or notification as described with reference to FIG. 16. In some instances, processing circuitry 50 may include the confidence interval value with the infection status, such as by applying a correction to the infection indication value depending on whether processing circuitry 50 determines a high confidence interval or low confidence interval that the increase or decrease in infection indication value is attributable to an infection at IMD 10 or not.

When T1 does not satisfy the predefined threshold of 1506, processing circuitry 50 may optionally indicate a normal status of patient 4 (NO branch from 1506 to 1510). Similarly, when T1 is not much greater than T2, processing circuitry 50 may optionally indicate a normal status of patient 4 (NO branch from 1512 to 1510). In any case, IMD 10 may continue monitoring patient 4 with or without indicating a status in such instances.

Processing circuitry 50 may determine whether T1 is much greater than T2, such as greater than T2 by more than a predefined threshold amount (1512). When T1 is greater than T2 by more than the predefined threshold amount, processing circuitry 50 may indicate a likely febrile event in patient 4 (YES branch to 1514). This may occur when patient 4 contracts a virus that causes an increase in core body temperature that leads to an increase in temperature at IMD 10. In such examples, T1 may increase before T2. For example, one or more temperature values from the first sensor, such as a body side sensor, may indicate an increasing body temperature before the second sensor, such as a skin side sensor, which may indicate a likely febrile event in patient 4. Where T1 is only greater than T2 by a lesser amount relative to the predefined threshold amount (NO branch from 1512 to 1510), processing circuitry 50 may optionally indicate a normal status (1510), as it will be expected that temperature values obtained from some bodily regions of patient 4 (e.g., core regions) will ordinarily be marginally higher than other regions (e.g., skin surface regions, muscle layers, etc.). It will be understood that T1 may represent temperature values from one or more sensors that are similarly situated (e.g., combined or averaged temperature values) and T2 may represent temperature values from one or more other sensors.

Figure 16:
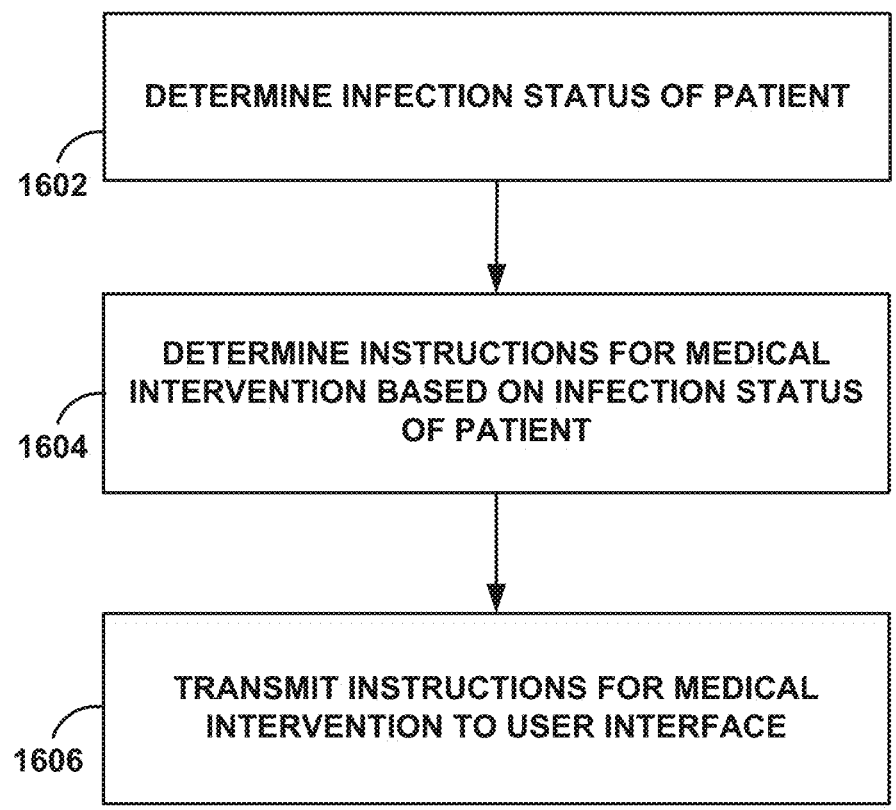
FIG. 16 is a flow diagram illustrating an example method that may be performed by one or both the IMD and external device shown in FIG. 1 to provide an alert to the patient with respect to an infection status of the patient, in accordance with one or more techniques disclosed herein.

Turning now to FIG. 16, external device 12 may receive the infection status of patient 4 from IMD 10 (1602). In some examples, external device 12 may determine the heart condition status and receive other data, such as raw temperature values, from processing circuitry 50. Although described as being generally performed by IMD 10, the example method of FIG. 16 may be performed by any of one or more of IMD 10, external device 12, or server 94, e.g., by the processing circuitry of any one or more of these devices.

External device 12 may determine instructions for medical intervention based on the infection status of patient 4 (1604). For example, if the infection indication value is greater than a predefined threshold, external device 12 may determine instructions for medical intervention based on an infection determination. In some examples, external device 12 may determine different instructions for different risk levels or categories. For example, external device 12 may determine a first set of instructions for an infection indication value being greater than a first threshold and a second set of instructions for an infection indication value being greater than a second threshold.

In some examples, external device 12 may not determine any instructions where an infection indication value may be tracking onto a rising core body temperature value. That is, in some instances, a rising core body temperature value may cause an increase in temperature of IMD 10. In such instances, an infection indication value may track onto the rising core body temperature value, which may not indicate a device pocket infection. In cases where the alert is configured to indicate an occurrence of a device pocket infection, processing circuitry, e.g., processing circuitry 50 of IMD 10, processing circuitry 80 of external device 12, processing circuitry 98 of external server 94, etc., may determine that the rise in temperature of IMD 10 is a result of an increase in core body temperature.

In some examples, external device 12 may provide an alert, such as a text- or graphics-based notification, a visual notification, etc. In some examples, external device 12 may sound an audible or tactile alarm for patient 4, alerting them of the determined level of risk. In other examples, external device 12 may provide a visual light indication, such as emitting a red light for high average device pocket temperature or a yellow light for medium average device pocket temperature.

In some examples, external device 12 may transmit the instructions for medical intervention to a user interface (1606). In some examples, external device 12 may transmit the instructions to a device of a caretaker, such as a pager. In examples where processing circuitry 50 generates the instructions based on the infection status, IMD 10 may transmit the instructions for medical intervention to a user interface. The instructions may include the infection indication value, temperature values, smoothened temperature values, etc. In some instances, a physician or caretaker may not need to know the actual temperature values and may only want to receive the infection status determined from the temperature values.

Various examples have been described. However, one skill in the art will appreciate that various modifications may be made to the described examples without departing from the scope of the claims. For example, one or more second indicators of infection may be used to determine whether the indication based on the first infection indicator is accurate as described in commonly-assigned U.S. application Ser. No. 11/737,173 by Gerber et al., entitled "INFECTION MONITORING," filed on Apr. 19, 2007, the content of which is incorporated herein by reference in its entirety.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, ROM, NVRAM, DRAM, SRAM, Flash memory, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Furthermore, although described primarily with reference to examples that provide an infection status to indicate a device pocket infection in response to detecting temperature changes in the device pocket, other examples may additionally or alternatively automatically modify a therapy in response to detecting the infection status in the patient. The therapy may be, as examples, a substance delivered by an implantable pump, a delivery of antibiotics, etc. These and other examples are within the scope of the following claims.

What is claimed is:

1. A system for determining an infection status of a patient, the system comprising:
an implantable medical device (IMD) comprising at least one temperature sensing device and being configured to be implanted in a patient; and
processing circuitry configured to:
determine, via the temperature sensing device, a first plurality of temperature values over time;
smooth the first plurality of temperature values determined over time to create a first smoothened temperature signal representing changes in the first plurality of temperature values over a first time period;
smooth the first plurality of temperature values determined over time to create a second smoothened temperature signal representing changes in the first plurality of temperature values over the first time period, the second smoothened temperature signal being different than the first smoothened temperature signal;
apply an infection detection model to the first smoothened temperature signal and the second smoothened temperature signal to determine an infection indication value, wherein to apply the infection detection model, the processing circuitry is configured to, compare the first smoothened temperature signal to the second smoothened temperature signal, and increase the infection indication value each time when the second smoothened temperature signal comprises a value that is greater than a corresponding value of the first smoothened temperature signal;
compare the infection indication value to a threshold;
determine, based at least in part on the infection indication value satisfying the threshold, an infection status of the patient;
generate at least one of an alert or instructions for medical intervention for output that is based at least in part on the infection status of the patient; and
transmit the alert or instructions for medical intervention to an external device for use by the patient, a caregiver, or a clinician.

2. The system of claim 1, wherein to smooth the first plurality of temperature values to create the first smoothened temperature signal, the processing circuitry is further configured to:
apply a first low pass filter to the first plurality of temperature values to create the first smoothened temperature signal over the first time period, the first low pass filter having a first cutoff frequency.

3. The system of claim 2, wherein to smooth the first plurality of temperature values to create the second smoothened temperature signal, the processing circuitry is further configured to:
apply a second low pass filter to the plurality of temperature values over the first time period to create the second smoothened temperature signal, the second low pass filter having a second cutoff frequency higher than the first cutoff frequency.

4. The system of claim 1, wherein the processing circuitry is further configured to:
reset the infection indication value to a baseline value each time when the second smoothened temperature signal comprises a value that is less than or equal to a corresponding value of the first smoothened temperature signal.

5. The system of claim 1, wherein the infection status indicates an infection in a device pocket of the IMD.

6. The system of claim 1, wherein the IMD comprises a second temperature sensor, wherein the processing circuitry is further configured to:
determine the first plurality of temperature values over time based at least in part on temperature measurements from at least the two temperature sensors included with the IMD.

7. The system of claim 1, wherein the processing circuitry is further configured to change a therapy to be delivered to the patient based at least in part on the infection indication value satisfying the threshold.

8. The system of claim 7, wherein the therapy comprises delivering a substance to the patient.

9. A method comprising:
determining, via a temperature sensing device of an implantable medical device (IMD) configured to be implanted in a patient, a first plurality of temperature values over time;
smoothing the first plurality of temperature values determined over time to create a first smoothened temperature signal representing changes in the first plurality of temperature values over a first time period;

smoothing the first plurality of temperature values determined over time to create a second smoothened temperature signal representing changes in the first plurality of temperature values over the first time period, the second smoothened temperature signal being different than the first smoothened temperature signal;

applying an infection detection model to the first smoothened temperature signal and the second smoothened temperature signal to determine an infection indication value, wherein applying the infection detection model comprises comparing the first smoothened temperature signal to the second smoothened temperature signal, and increase an infection indication value each time when the second smoothened temperature signal comprises a value that is greater than a corresponding value of the first smoothened temperature signal;

comparing the infection indication value to a threshold;

determining, based at least in part on the infection indication value satisfying the threshold, an infection status of the patient;

generating at least one of an alert or instructions for medical intervention for output that is based at least in part on the infection status of the patient; and transmitting the alert or instructions for medical intervention to an external device for use by the patient, a caregiver, or a clinician.

10. The method of claim 9, wherein smoothing the first plurality of temperature values to create the first smoothened temperature signal comprises:

applying a first low pass filter to the first plurality of temperature values to create the first smoothened temperature signal over the first time period, the first low pass filter having a first cutoff frequency.

11. The method of claim 10, wherein smoothing the first plurality of temperature values to create the second smoothened temperature signal comprises:

applying a second low pass filter to the first plurality of temperature values over the first time period to create the second smoothened temperature signal, the second low pass filter having a second cutoff frequency higher than the first cutoff frequency.

12. The method of claim 9, wherein the infection status indicates an infection in a device pocket of the IMD.

13. The method of claim 9, wherein the IMD comprises a second temperature sensor, wherein the method further comprises:

determining the first plurality of temperature values over time based at least in part on temperature measurements from at least the two temperature sensors included with the IMD.

14. The method of claim 9, further comprising:

resetting the infection indication value to a baseline value when the second smoothened temperature signal comprises a value that is less than or equal to a corresponding value of the first smoothened temperature signal.

15. The method of claim 9, further comprising changing a therapy to be delivered to the patient based at least in part on the infection indication value satisfying the threshold.

16. The method of claim 15, wherein the therapy comprises delivering a substance to the patient.

17. A non-transitory computer-readable storage medium having stored thereon instructions that, when executed, cause one or more processors to at least:

determine, via a temperature sensing device of an implantable medical device (IMD) configured to be implanted in a patient, a first plurality of temperature values over time;

smooth the first plurality of temperature values determined over time to create a first smoothened temperature signal representing changes in the first plurality of temperature values over a first time period;

smooth the first plurality of temperature values determined over time to create a second smoothened temperature signal representing changes in the first plurality of temperature values over the first time period, the second smoothened temperature signal being different than the first smoothened temperature signal;

apply an infection detection model to the first smoothened temperature signal and the second smoothened temperature signal to determine an infection indication value, wherein the instructions cause the one or more processors to apply the infection detection model by comparing the first smoothened temperature signal to the second smoothened temperature signal, and increasing the infection indication value each time when the second smoothened temperature signal comprises a value that is greater than a corresponding value of the first smoothened temperature signal;

compare the infection indication value to a threshold;

determine, based at least in part on the infection indication value satisfying the threshold, an infection status of the patient;

generate at least one of an alert or instructions for medical intervention for output that is based at least in part on the infection status of the patient; and transmit the alert or instructions for medical intervention to an external device for use by the patient, a caregiver, or a clinician.

* * * * *